United States Patent
Zamierowski

(10) Patent No.: US 7,351,250 B2
(45) Date of Patent: Apr. 1, 2008

(54) CIRCUMFERENTIAL MEDICAL CLOSURE DEVICE AND METHOD

(75) Inventor: David S. Zamierowski, Shawnee Mission, KS (US)

(73) Assignee: KCI Licensing, Inc., San Antonio, TX (US)

( * ) Notice: Subject to any disclaimer, the term of this patent is extended or adjusted under 35 U.S.C. 154(b) by 408 days.

(21) Appl. No.: 11/103,043

(22) Filed: Apr. 11, 2005

(65) Prior Publication Data

US 2005/0182445 A1 Aug. 18, 2005

Related U.S. Application Data

(63) Continuation-in-part of application No. 10/224,852, filed on Aug. 21, 2002.

(51) Int. Cl.
*A61B 17/08* (2006.01)
*A61D 1/00* (2006.01)

(52) U.S. Cl. ..................................... 606/215
(58) Field of Classification Search ......... 606/213–221
See application file for complete search history.

(56) References Cited

U.S. PATENT DOCUMENTS

| 221,427 | A | 11/1879 | Sherman |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,969,057 | A | 1/1961 | Simmons |
| 3,066,672 | A | 12/1962 | Crosby, Jr. et al. |
| 3,115,138 | A | 12/1963 | McEvenny et al. |

(Continued)

FOREIGN PATENT DOCUMENTS

AU 550575 A1 8/1982

(Continued)

OTHER PUBLICATIONS

Mendez-Eastman, Susan. When Wounds Won't Heal, Jan. 1998. RN, pp. 20-23.*

(Continued)

*Primary Examiner*—Michael J. Hayes
*Assistant Examiner*—Christina Gettman

(57) ABSTRACT

A flexible medical closure screen device for a separation of first and second tissue portions is provided, which includes a mesh screen comprising tubular vertical risers, vertical strands with barbed filaments, and horizontal spacers connecting the risers and strands in a grid-like configuration. An optional perimeter member partly surrounds the screen and can comprise a perimeter tube fluidically coupled with the vertical risers to form a tubing assembly. Various input/output devices can optionally be connected to the perimeter tube ends for irrigating and/or draining the separation according to methodologies of the present invention. Separation closure, irrigation and drainage methodologies are disclosed utilizing various combinations of closure screens, tubing, sutures, fluid transfer elements and gradient force sources. The use of mechanical forces associated with barbed strands for repositionably securing separated tissues together is disclosed. The use of same for eliminating or reducing the formation of subcutaneous voids or pockets, which can potentially form hematoma and seroma effects, is also disclosed. Alternative embodiments of the invention have circumferential configurations for approximating and closing separated tissue portions such as tendons, nerves and blood vessels. Tissue closure methods include the steps of circumferentially applying a screen to separated tissue portions and penetrating the tissue portions with prongs.

12 Claims, 36 Drawing Sheets

U.S. PATENT DOCUMENTS

| | | |
|---|---|---|
| 3,367,332 A | 2/1968 | Groves |
| 3,520,300 A | 7/1970 | Flower |
| 3,648,692 A | 3/1972 | Wheeler |
| 3,682,180 A | 8/1972 | McFarlane |
| 3,826,254 A | 7/1974 | Mellor |
| 3,981,051 A * | 9/1976 | Brumlik ................ 24/447 |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,233,969 A | 11/1980 | Lock et al. |
| 4,245,630 A | 1/1981 | Lloyd et al. |
| 4,248,232 A | 2/1981 | Engelbrecht et al. |
| 4,259,959 A * | 4/1981 | Walker ................ 606/221 |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman et al. |
| 4,392,853 A | 7/1983 | Muto |
| 4,392,858 A | 7/1983 | George et al. |
| 4,419,093 A | 12/1983 | Deaton |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,696,301 A | 9/1987 | Barabe |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,976,726 A | 12/1990 | Haverstock |
| 4,985,019 A | 1/1991 | Michelson |
| 5,007,921 A | 4/1991 | Brown |
| 5,007,936 A | 4/1991 | Woolson |
| 5,019,083 A | 5/1991 | Klapper et al. |
| 5,037,397 A | 8/1991 | Kalt et al. |
| 5,045,054 A | 9/1991 | Hood et al. |
| 5,086,170 A | 2/1992 | Luheshi et al. |
| 5,092,858 A | 3/1992 | Benson et al. |
| 5,100,396 A | 3/1992 | Zamierowski |
| 5,112,338 A | 5/1992 | Anspach, III |
| 5,134,994 A | 8/1992 | Say |
| 5,149,331 A | 9/1992 | Ferdman et al. |
| 5,167,613 A | 12/1992 | Karami et al. |
| 5,169,399 A | 12/1992 | Ryland et al. |
| 5,176,663 A | 1/1993 | Svedman et al. |
| 5,215,522 A | 6/1993 | Page et al. |
| D337,639 S | 7/1993 | Beckman |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,291,887 A | 3/1994 | Stanley et al. |
| 5,298,015 A | 3/1994 | Komatsuzaki et al. |
| 5,318,570 A | 6/1994 | Hood et al. |
| 5,342,376 A | 8/1994 | Ruff |
| 5,344,415 A | 9/1994 | DeBusk et al. |
| 5,358,494 A | 10/1994 | Svedman |
| 5,383,897 A | 1/1995 | Wholey |
| 5,423,885 A * | 6/1995 | Williams ................ 623/1.17 |
| 5,437,622 A | 8/1995 | Carion |
| 5,437,651 A | 8/1995 | Todd et al. |
| 5,507,833 A | 4/1996 | Bohn |
| 5,522,901 A | 6/1996 | Thomas et al. |
| 5,527,293 A | 6/1996 | Zamierowski |
| D372,309 S | 7/1996 | Heldreth |
| 5,549,584 A | 8/1996 | Gross |
| 5,556,375 A | 9/1996 | Ewall |
| 5,580,353 A | 12/1996 | Mendes et al. |
| 5,584,859 A | 12/1996 | Brotz |
| 5,607,388 A | 3/1997 | Ewall |
| 5,630,819 A | 5/1997 | Ashby et al. |
| 5,636,643 A | 6/1997 | Argenta et al. |
| 5,645,081 A | 7/1997 | Argenta et al. |
| 5,716,360 A | 2/1998 | Baldwin et al. |
| 5,738,686 A | 4/1998 | Bubein-Meesenburg et al. |
| 5,785,700 A | 7/1998 | Olson |
| 5,800,546 A | 9/1998 | Marik et al. |
| 5,827,246 A | 10/1998 | Bowen |
| 5,846,244 A | 12/1998 | Cripe |
| 5,911,222 A | 6/1999 | Lawrence et al. |
| 5,921,972 A | 7/1999 | Skow |
| 5,931,855 A | 8/1999 | Buncke |
| 5,941,859 A | 8/1999 | Lerman |
| 6,071,267 A | 6/2000 | Zamierowski |
| 6,113,618 A | 9/2000 | Nic |
| 6,126,659 A | 10/2000 | Wack |
| 6,135,116 A | 10/2000 | Vogel et al. |
| 6,142,982 A | 11/2000 | Hunt et al. |
| 6,146,423 A | 11/2000 | Cohen et al. |
| 6,159,246 A | 12/2000 | Mendes et al. |
| 6,174,306 B1 | 1/2001 | Fleischmann |
| 6,179,804 B1 | 1/2001 | Satterfield |
| 6,190,391 B1 | 2/2001 | Stubbs |
| 6,190,392 B1 | 2/2001 | Vandewalle et al. |
| 6,203,563 B1 | 3/2001 | Fernandez |
| 6,241,747 B1 | 6/2001 | Ruff |
| 6,270,517 B1 | 8/2001 | Brotz |
| RE37,358 E | 9/2001 | Del Rio et al. |
| 6,287,316 B1 | 9/2001 | Agarwal et al. |
| 6,293,929 B1 | 9/2001 | Smith et al. |
| 6,345,623 B1 | 2/2002 | Heaton et al. |
| 6,355,215 B1 | 3/2002 | Poggie et al. |
| 6,377,653 B1 | 4/2002 | Lee et al. |
| 6,398,767 B1 | 6/2002 | Fleischmann |
| 6,430,427 B1 | 8/2002 | Lee et al. |
| 6,488,643 B1 | 12/2002 | Tumey et al. |
| 6,493,568 B1 | 12/2002 | Bell et al. |
| 6,500,209 B1 | 12/2002 | Kolb |
| 6,503,281 B1 | 1/2003 | Mallory |
| 6,553,998 B2 | 4/2003 | Heaton et al. |
| 6,620,132 B1 | 9/2003 | Skow |
| 6,626,891 B2 | 9/2003 | Ohmstede |
| 6,645,226 B1 | 11/2003 | Jacobs et al. |
| 6,669,735 B1 | 12/2003 | Pelissier |
| 6,685,681 B2 | 2/2004 | Lockwood et al. |

| | | |
|---|---|---|
| 6,695,823 B1 | 2/2004 | Lina et al. |
| 6,726,706 B2 | 4/2004 | Dominguez |
| 6,752,794 B2 | 6/2004 | Lockwood et al. |
| 6,800,074 B2 | 10/2004 | Henley et al. |
| 6,814,079 B2 | 11/2004 | Heaton et al. |
| 6,991,643 B2 * | 1/2006 | Saadat ..................... 606/221 |
| 2002/0022861 A1 * | 2/2002 | Jacobs et al. ............... 606/216 |
| 2002/0029063 A1 | 3/2002 | Wittman |
| 2002/0029083 A1 | 3/2002 | Wittmann |
| 2002/0077661 A1 | 6/2002 | Saadat |
| 2002/0099447 A1 | 7/2002 | Mears et al. |
| 2002/0115951 A1 | 8/2002 | Norstrem et al. |
| 2002/0116067 A1 | 8/2002 | Mears et al. |
| 2002/0120185 A1 | 8/2002 | Johnson |
| 2002/0143286 A1 | 10/2002 | Turney |
| 2002/0183565 A1 | 12/2002 | Leavanoni et al. |
| 2003/0050594 A1 | 3/2003 | Zamierowski |
| 2003/0097135 A1 | 5/2003 | Penenberg |
| 2004/0039415 A1 | 2/2004 | Zamierowski |
| 2005/0043818 A1 | 2/2005 | Caneiro et al. |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358 302 A2 | 3/1990 |
| EP | 1 018 967 B1 | 8/2004 |
| GB | 692578 | 6/1953 |
| GB | 2 197 789 A | 6/1988 |
| GB | 2 220 357 A | 1/1990 |
| GB | 2 235 877 A | 3/1991 |
| GB | 2333965 A | 8/1999 |
| GB | 2329127 B | 8/2000 |
| JP | 4129536 | 4/1992 |
| SG | 71559 | 4/2002 |
| WO | WO 80/02182 | 10/1980 |
| WO | WO 93/09727 | 5/1993 |
| WO | WO 94/20041 | 9/1994 |
| WO | WO96/05873 | 2/1996 |
| WO | WO97/18007 | 5/1997 |
| WO | WO 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 4, 1986; pp. 66-70, and 9 page English translation thereof.

Yusupov. Yu. N.. et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980; pp. 132-136, and 8 page English translation thereof.

* cited by examiner

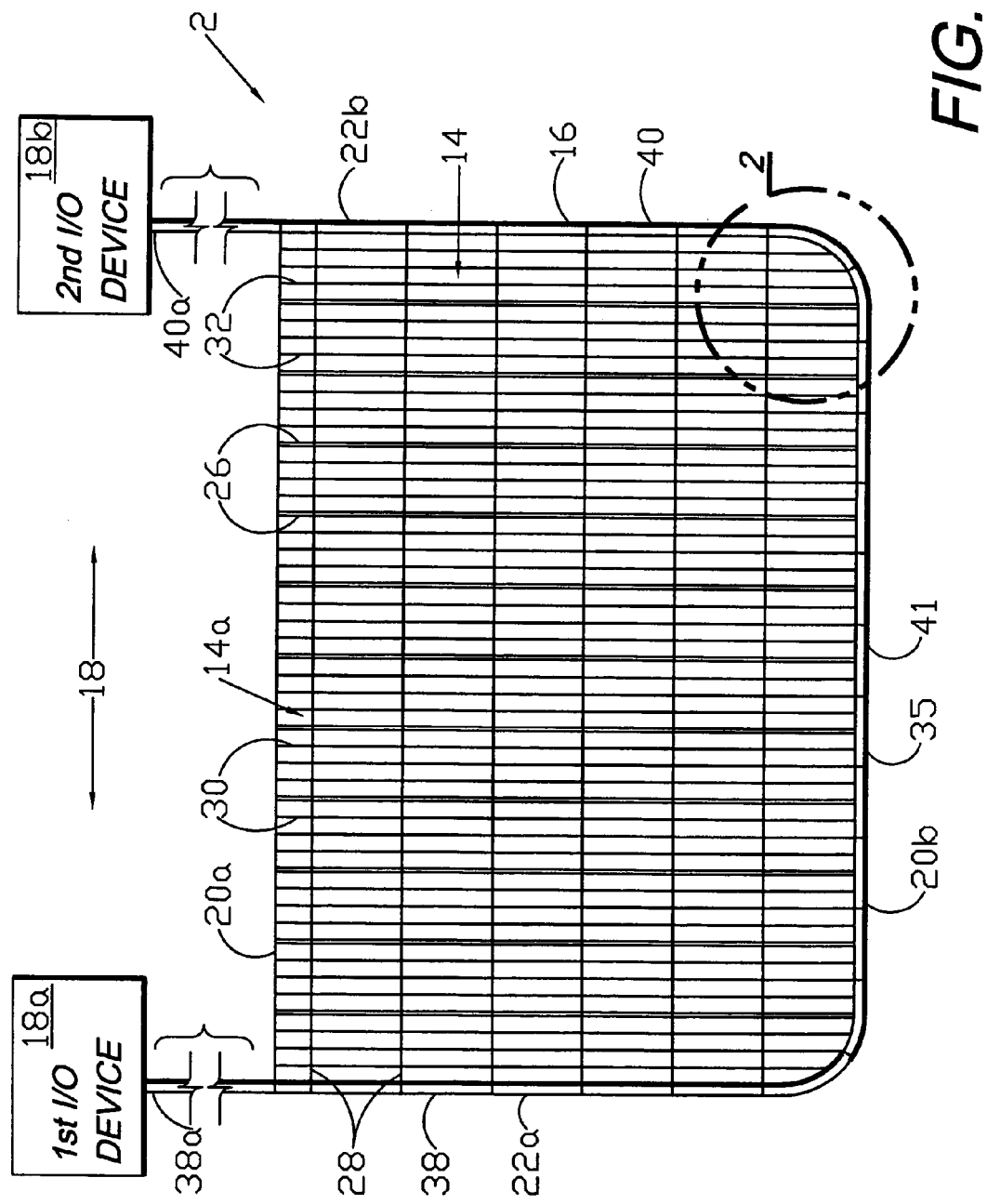

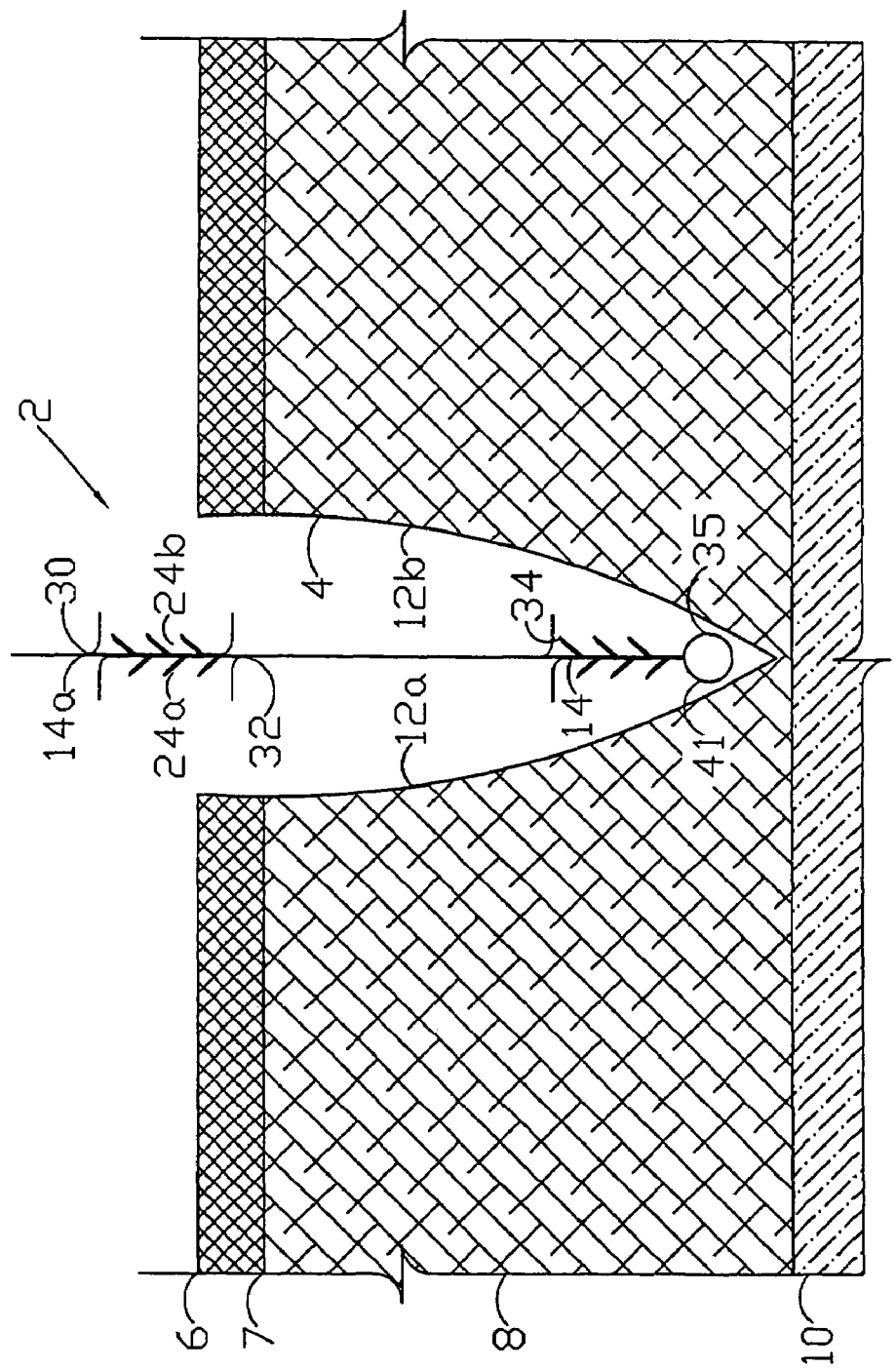

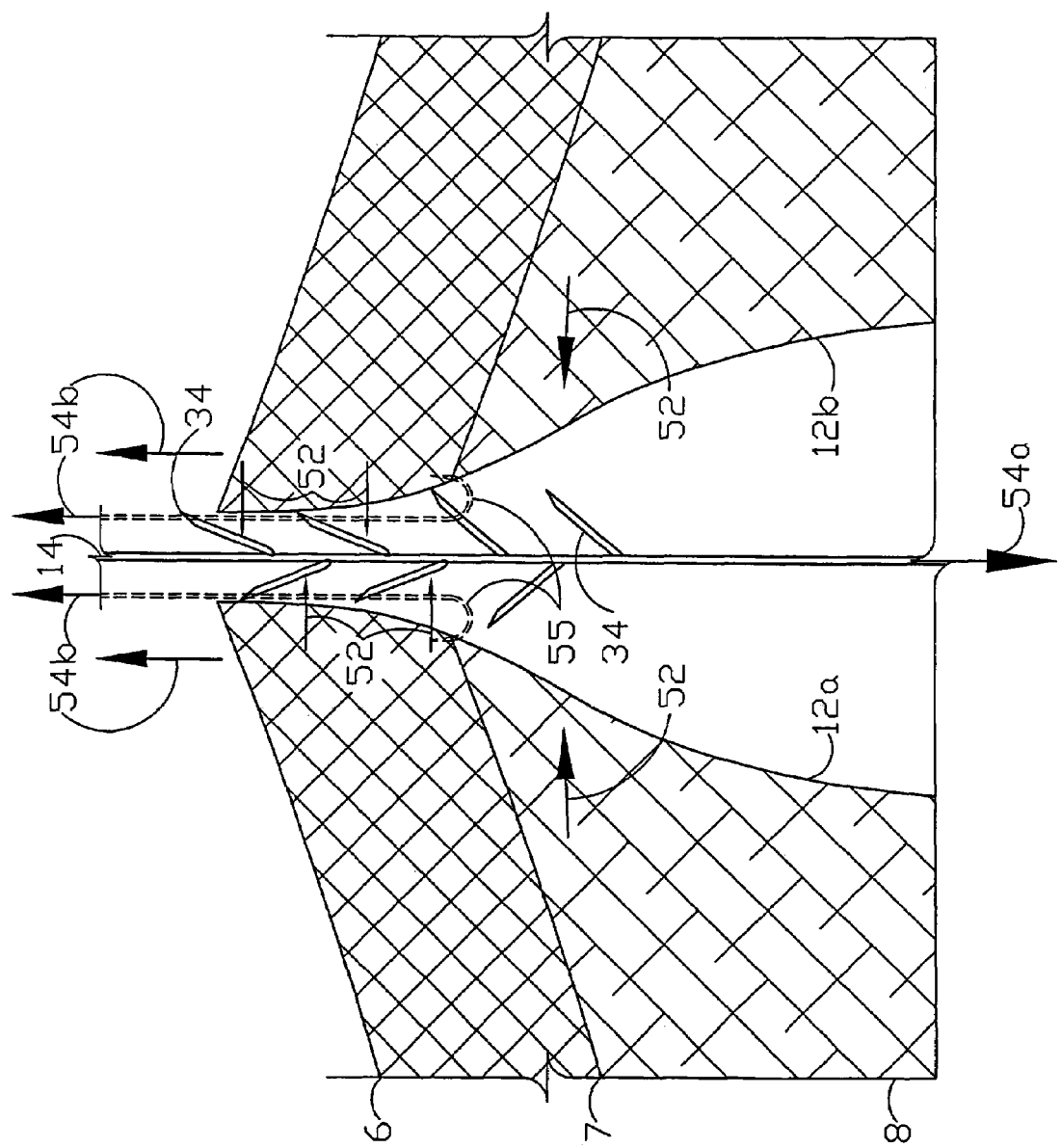

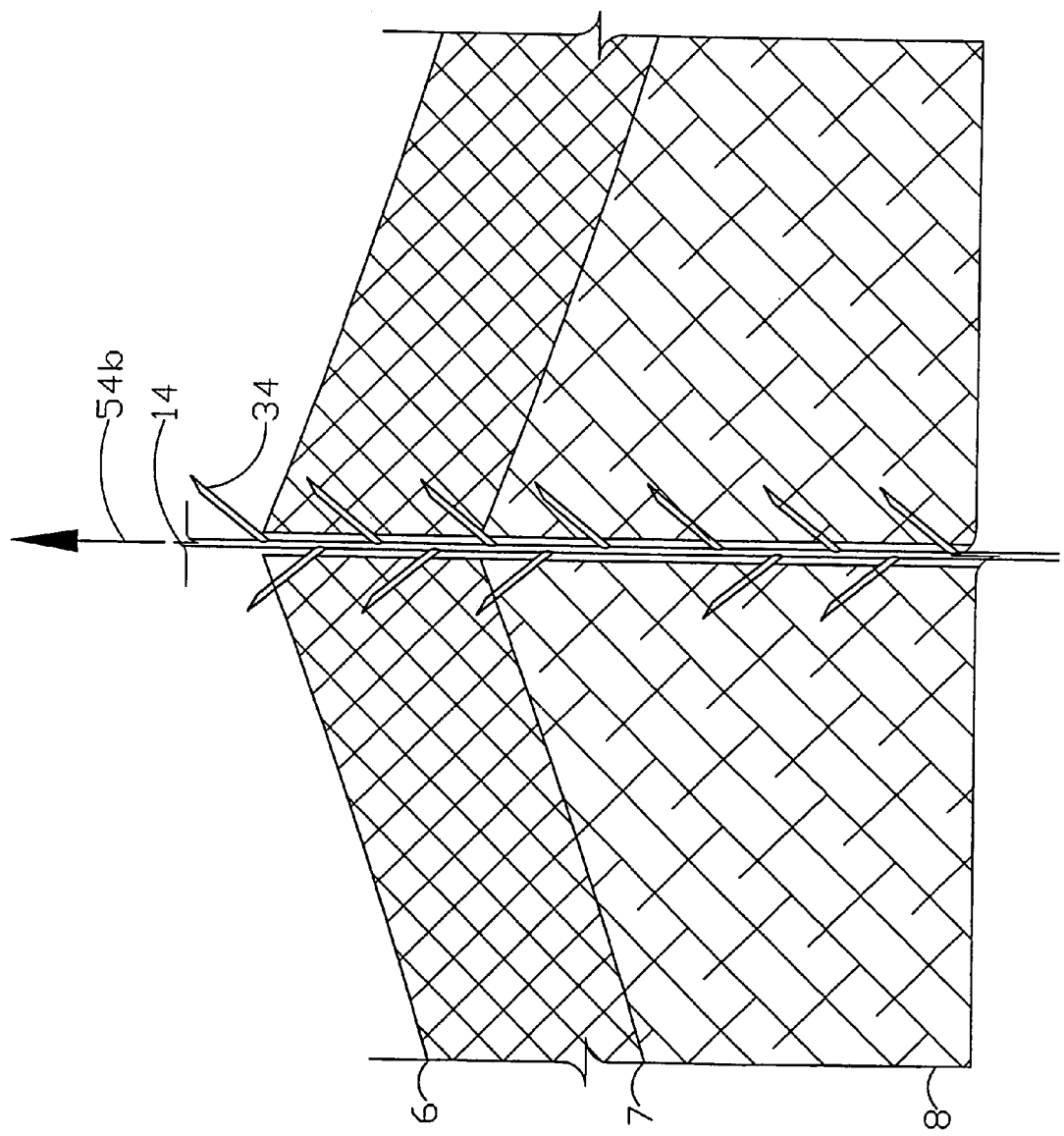

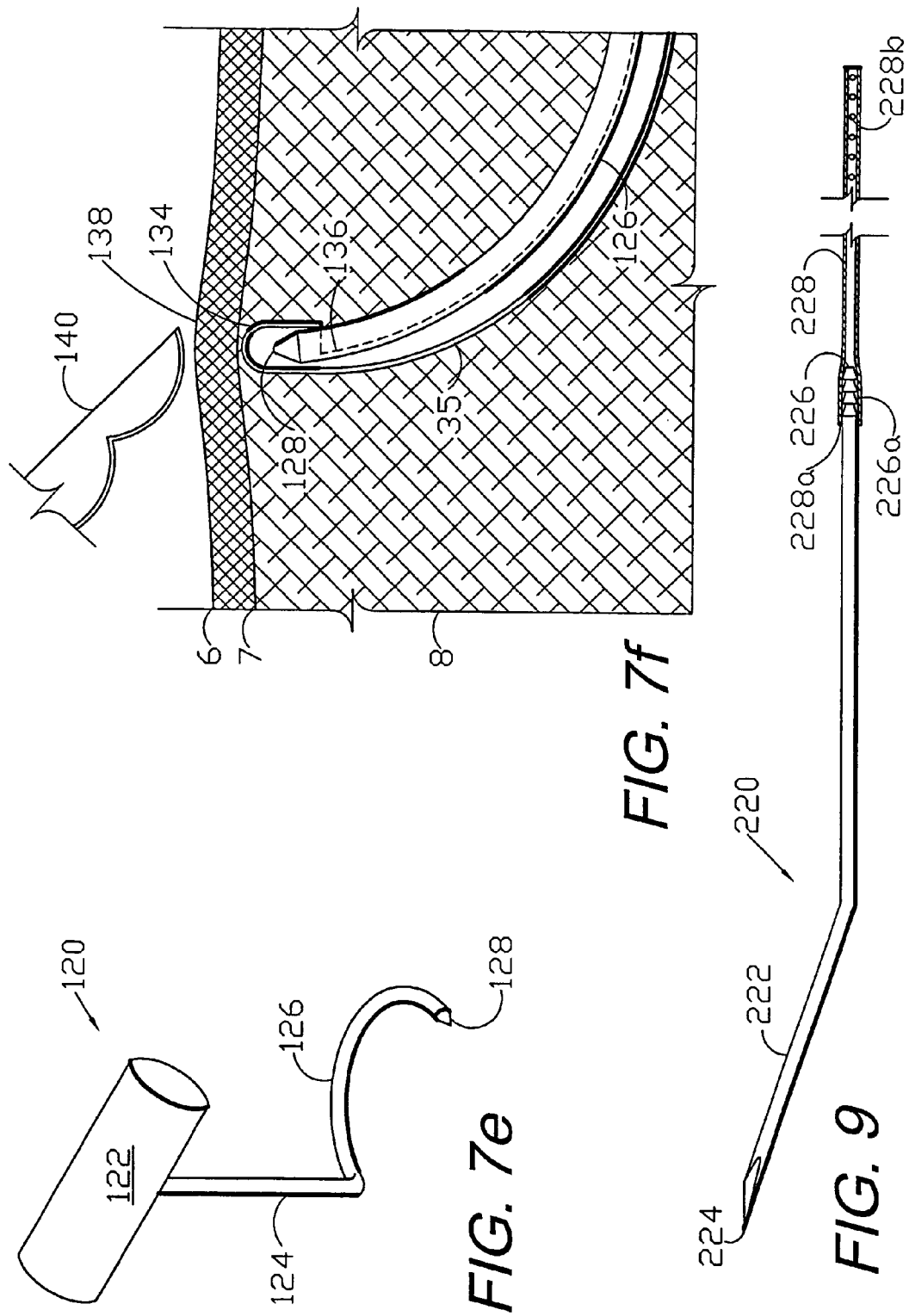

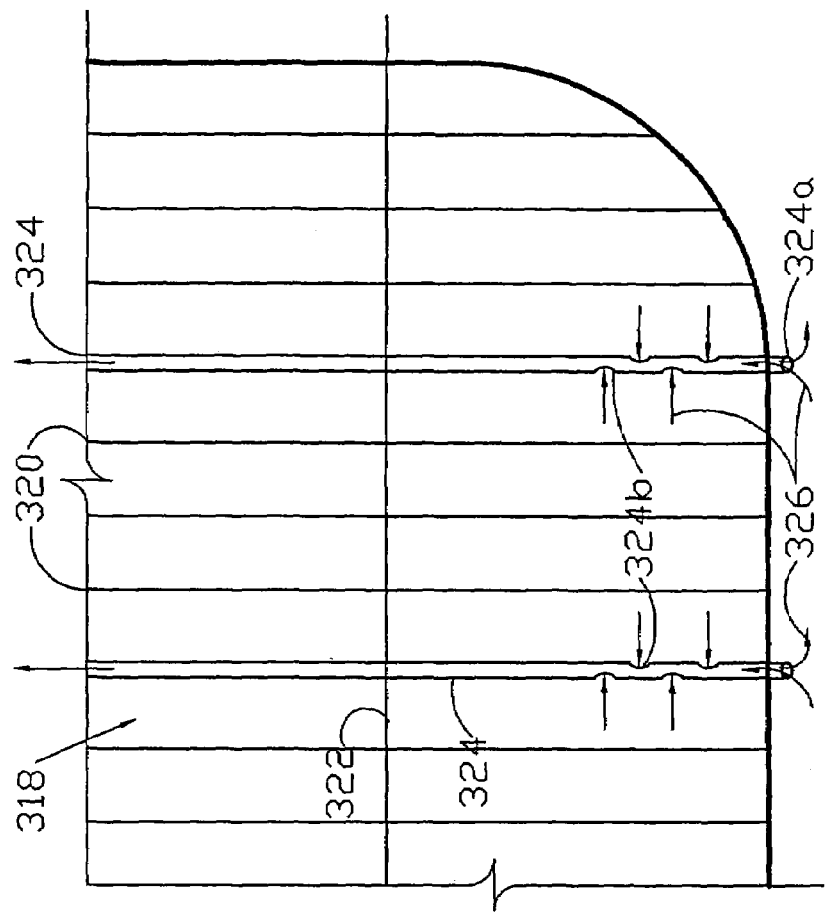
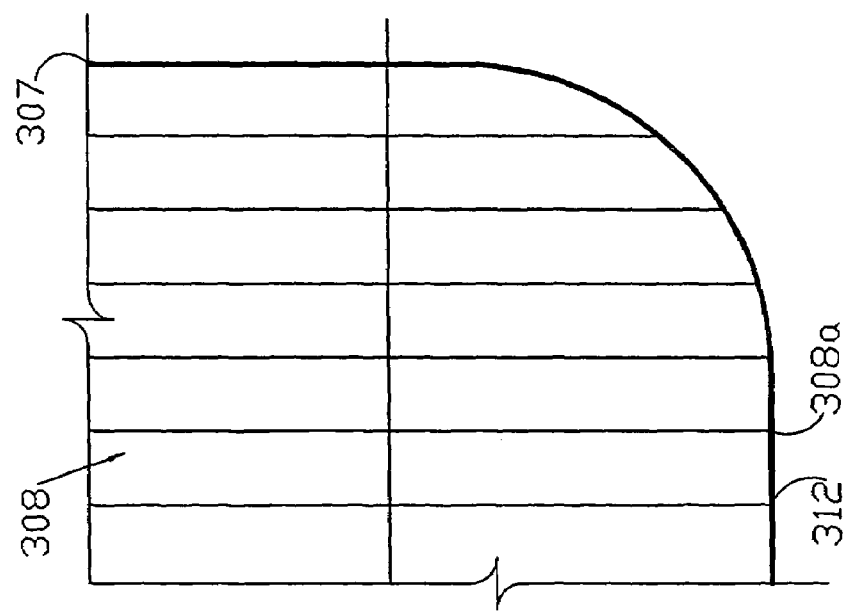

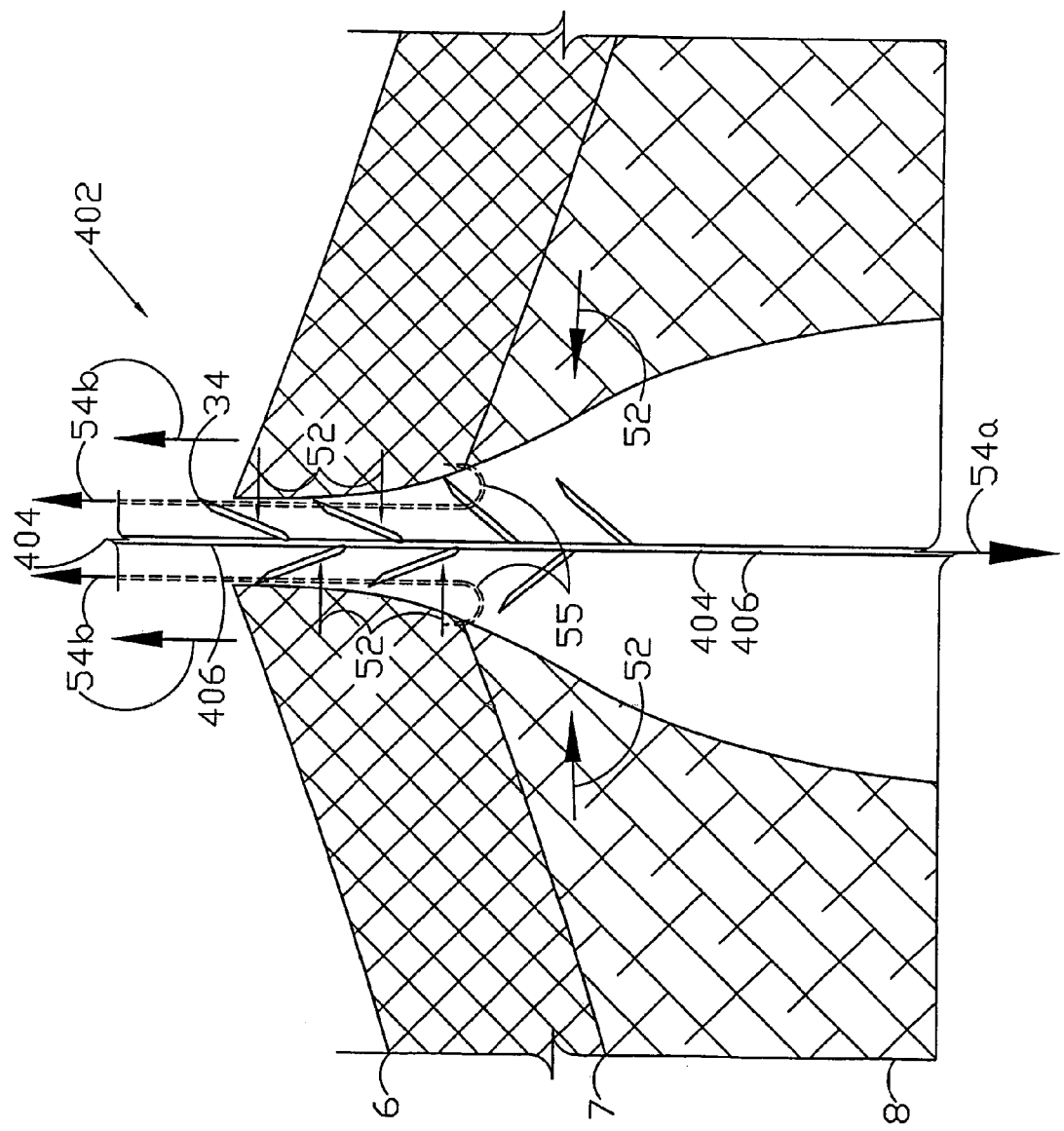

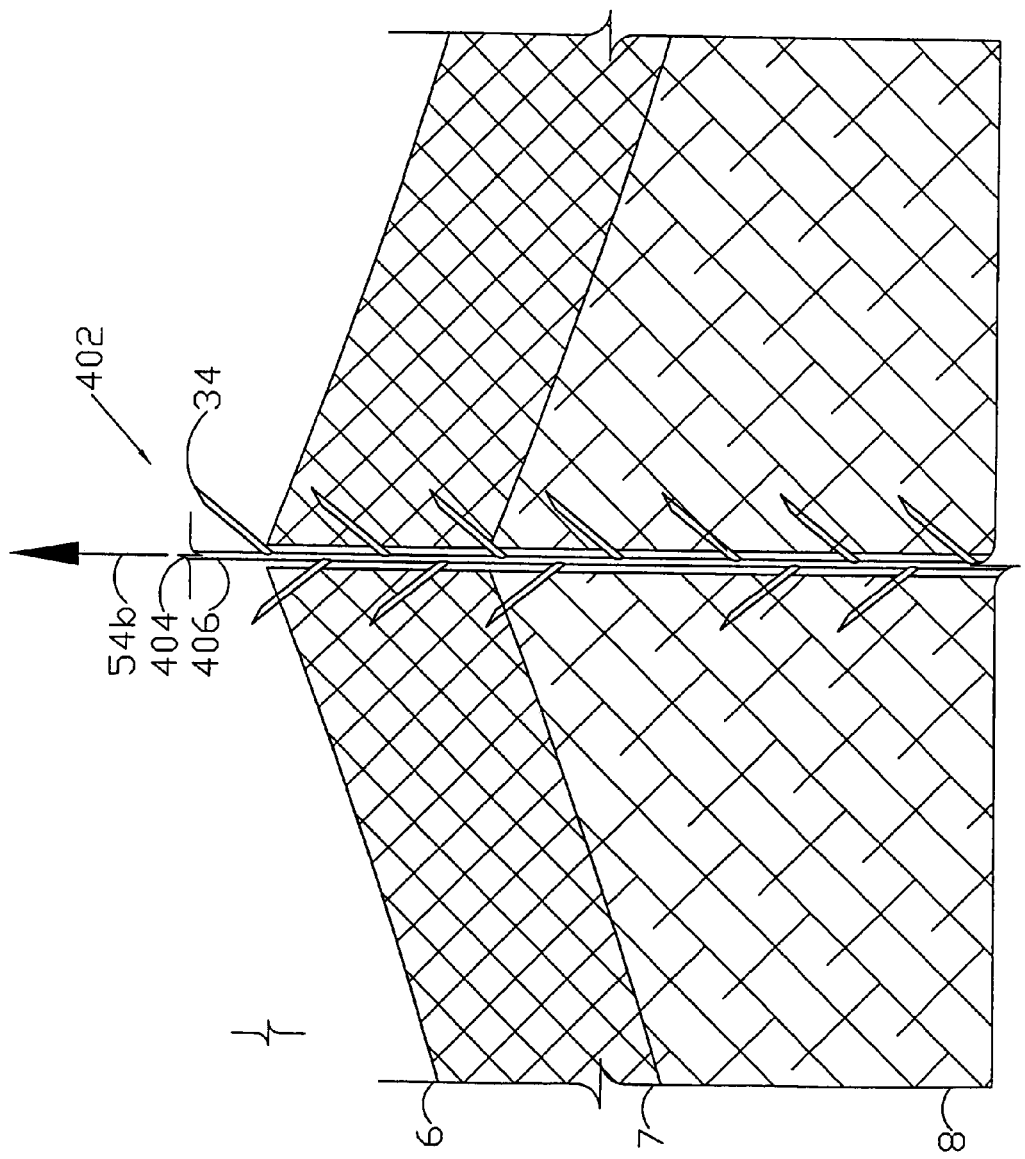

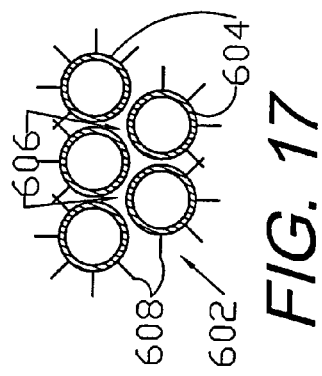
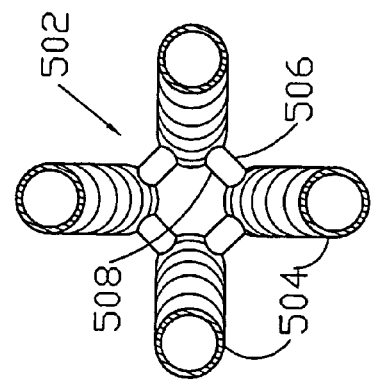
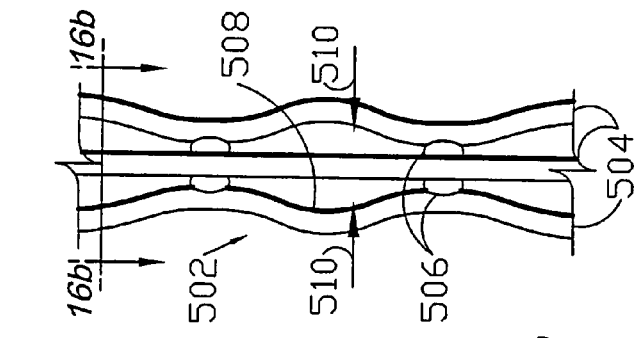
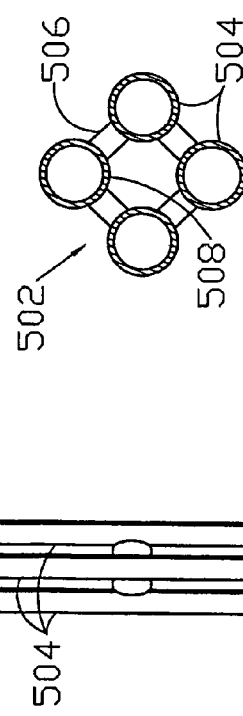
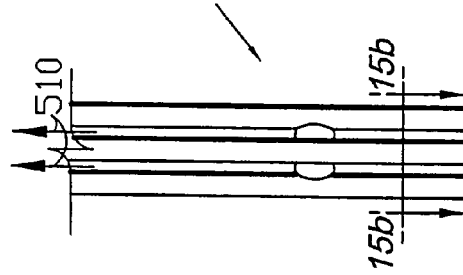

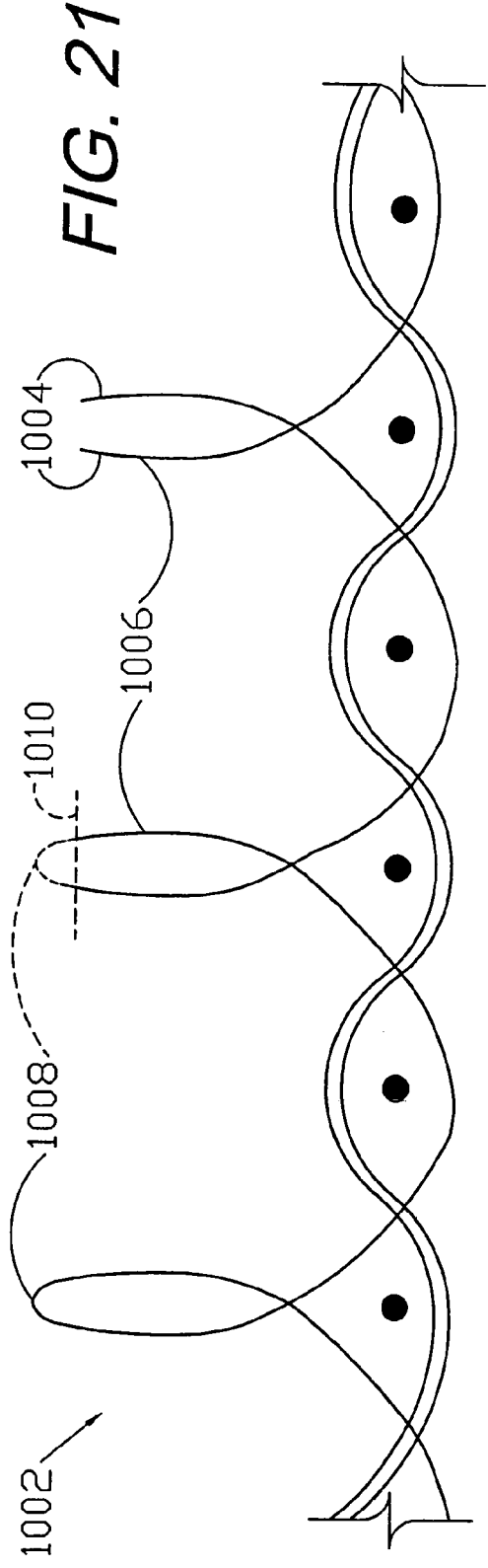
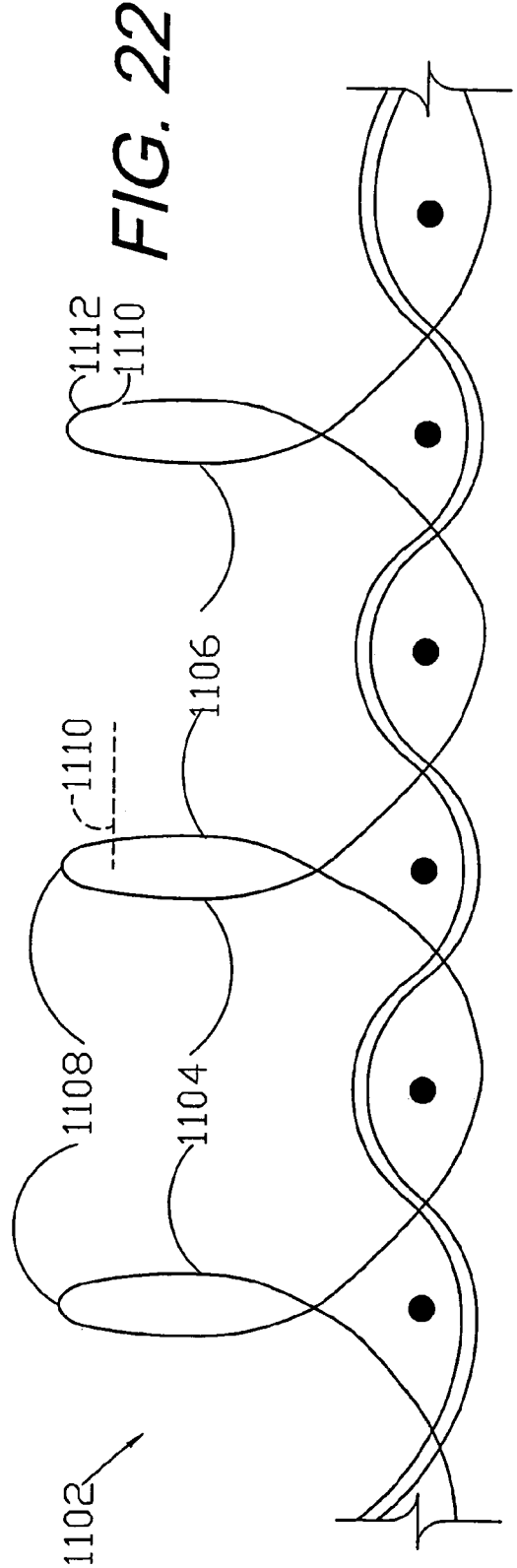

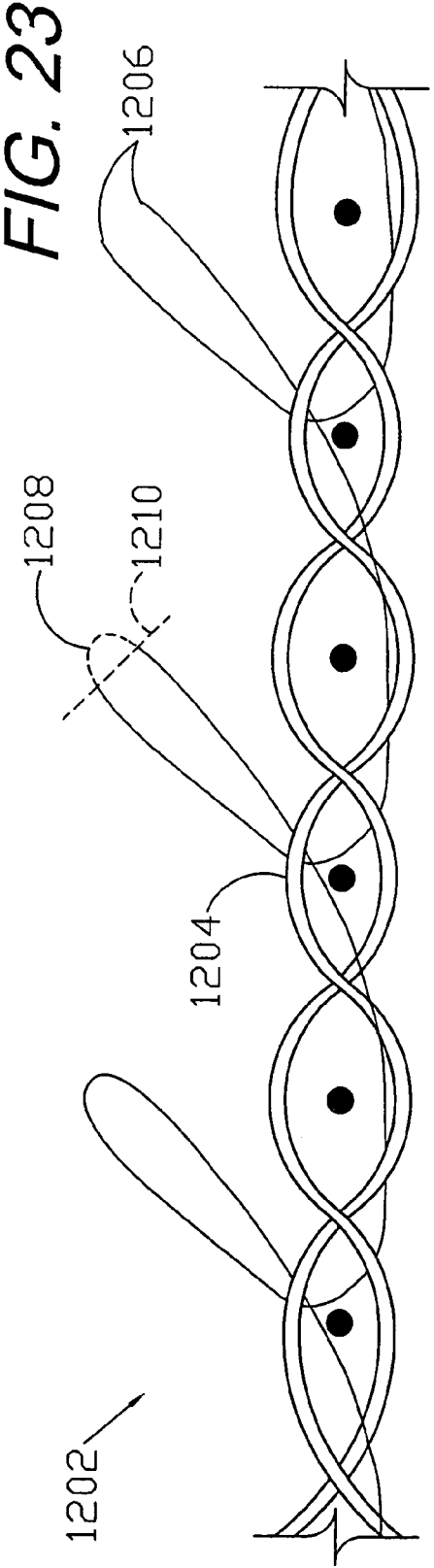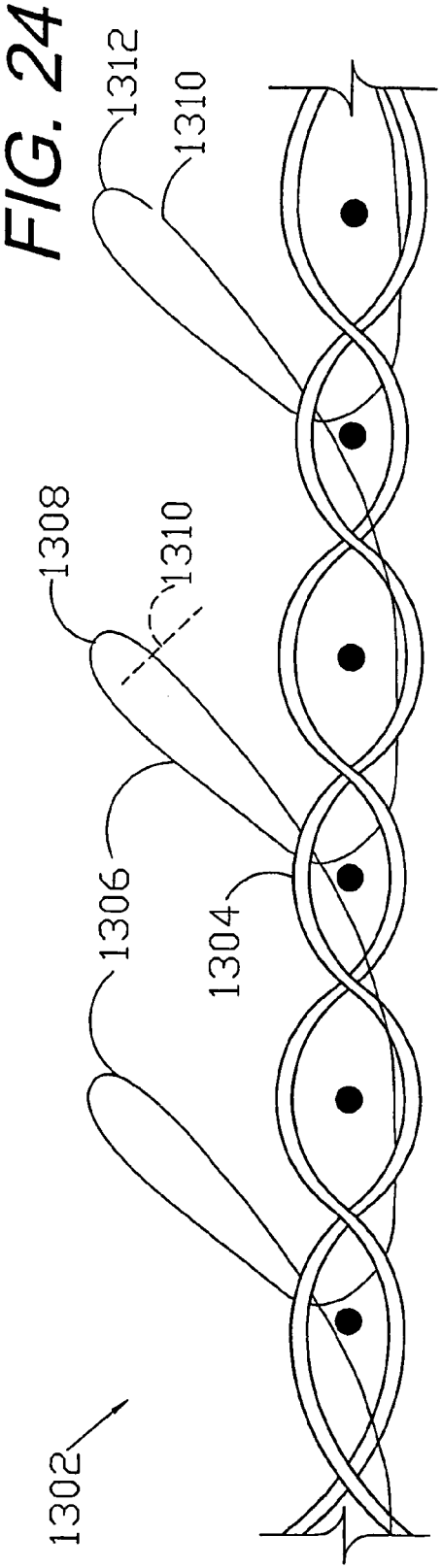

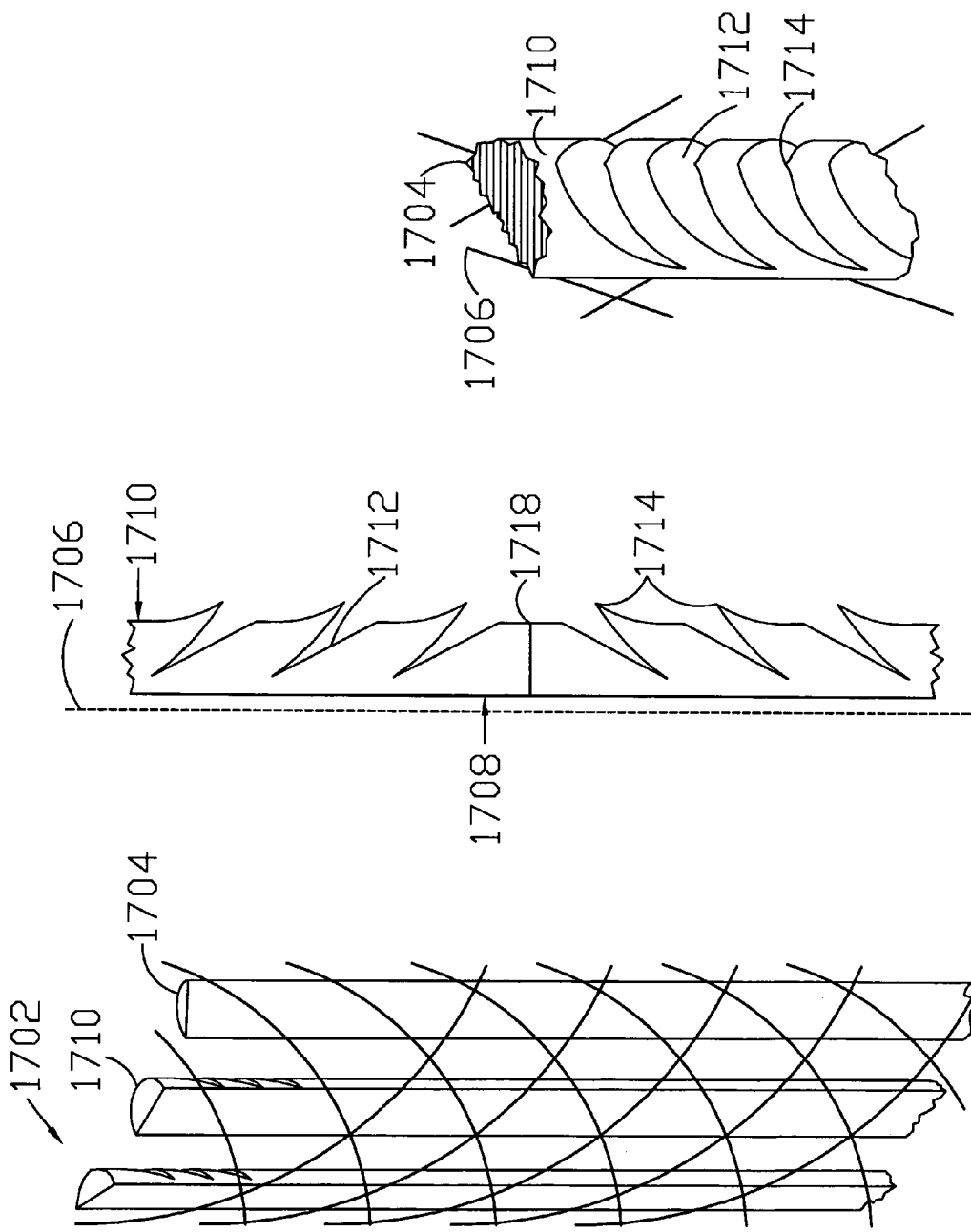

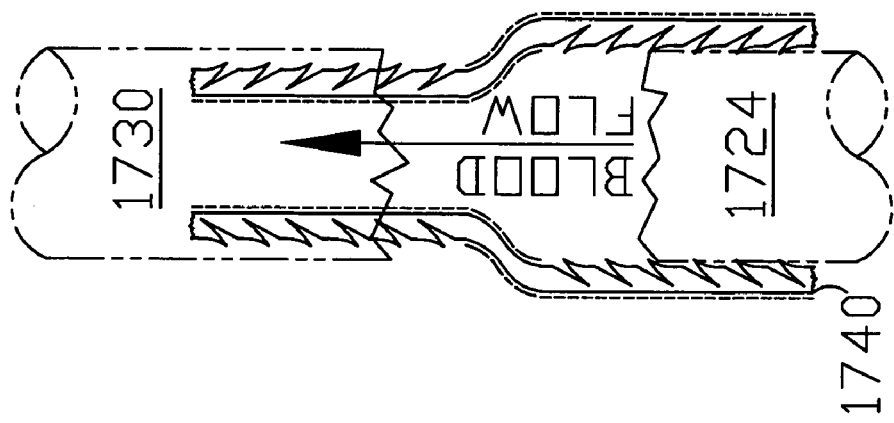
FIG. 32
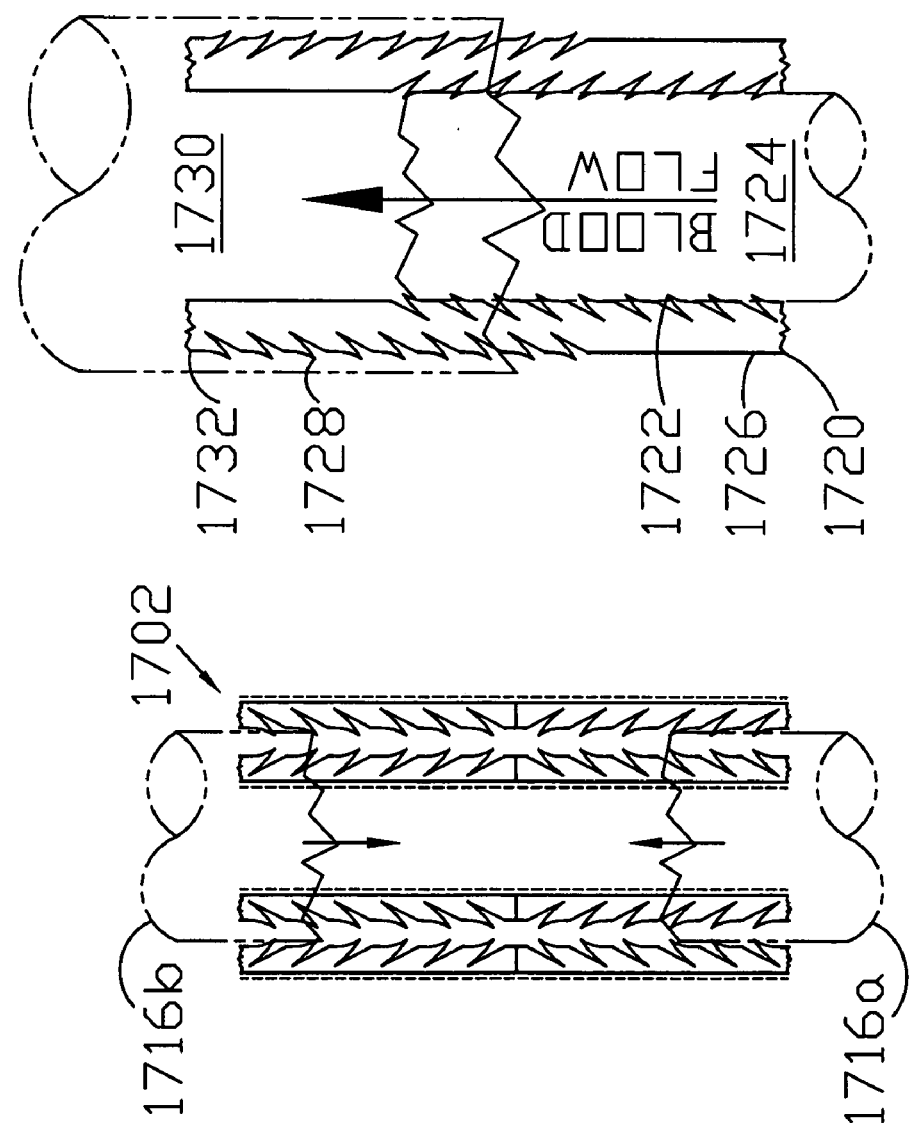
FIG. 31a
FIG. 31

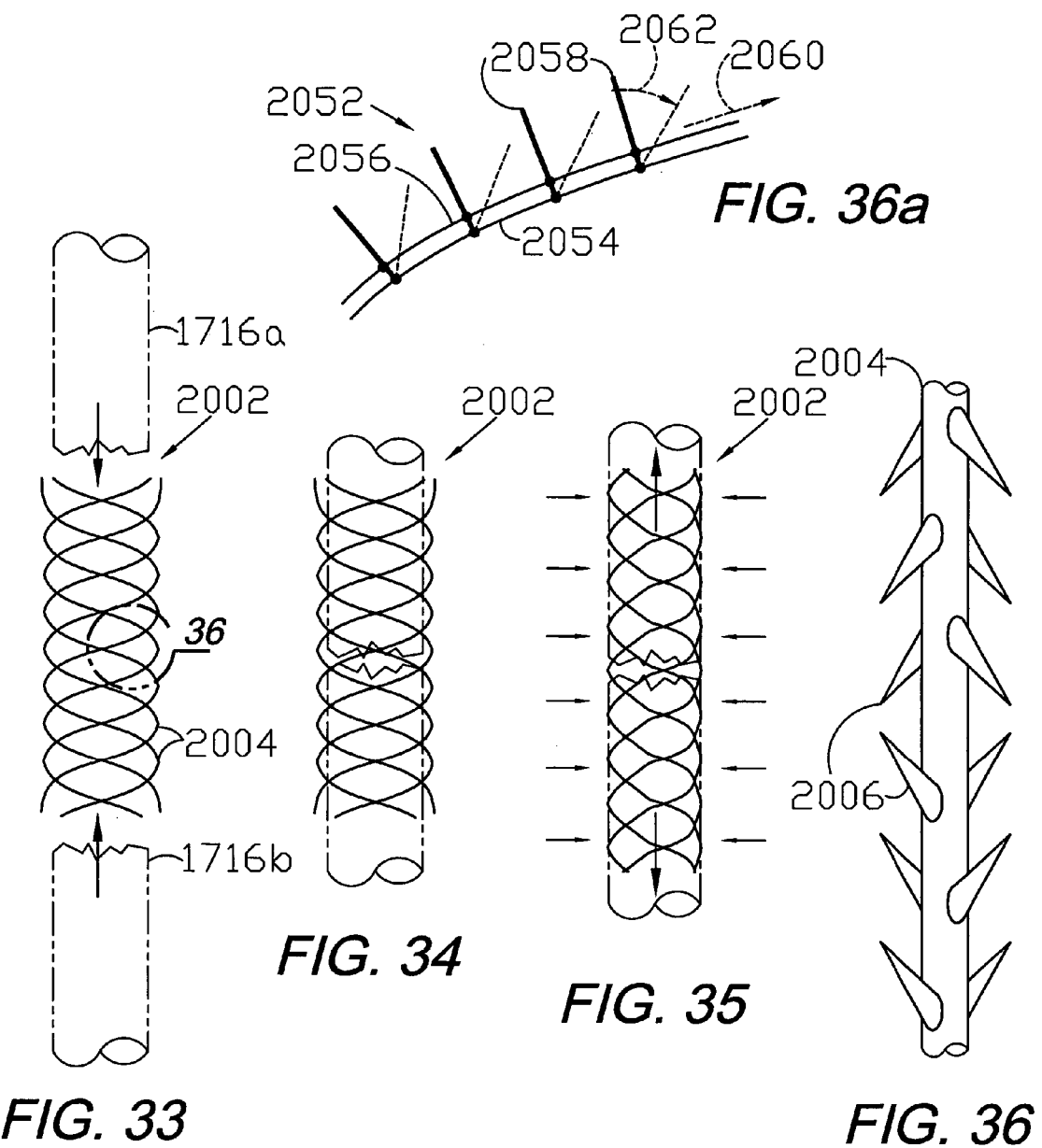

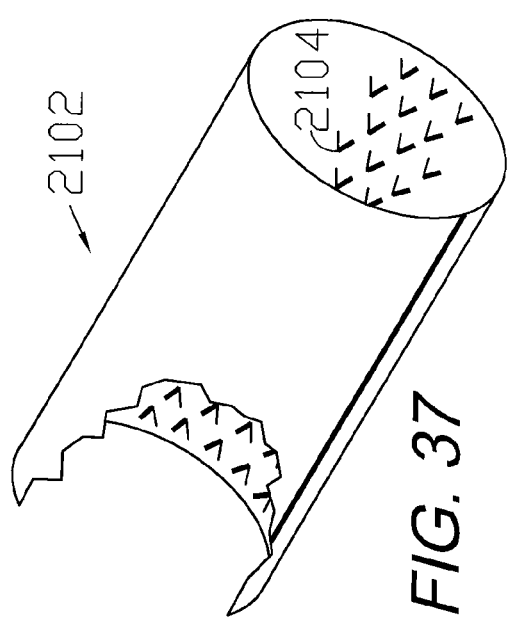
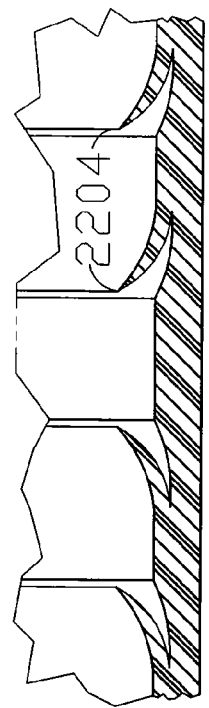
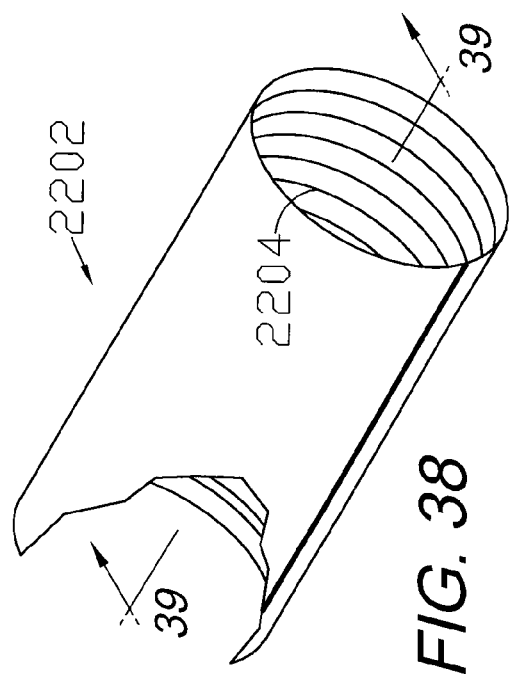

CIRCUMFERENTIAL MEDICAL CLOSURE DEVICE AND METHOD

CROSS-REFERENCE TO RELATED APPLICATION

This application is a continuation-in-part of U.S. patent application Ser. No. 10/224,852 filed on Aug. 21, 2002 currently pending in the United States Patent Office, and is incorporated herein by reference.

BACKGROUND OF THE INVENTION

1. Field of the Invention

The present invention relates generally to medical closure and wound fluid management devices and methods, and in particular to a circumferential device for linear tissue closure applications, such as reconstructing blood vessels, nerves, tendons, etc., which closure device is optionally bioabsorbable.

2. Description of the Prior Art

In the medical field, which is broadly defined to include dentistry, veterinary medicine, etc., cutaneous incisions are commonly performed in surgery to provide access to underlying tissue, organs, joints, skeletal structure, etc. Incision and closure techniques are an important part of surgery in general. They tend to occupy surgical teams and other resources for significant portions of many surgical procedures.

Surgeons generally strive to minimize the traumatic and scarring effects of surgery on their patients by both minimizing the incisions, and by employing a variety of closure techniques which tend to reduce postoperative swelling, bleeding, seroma, infection and other undesirable postoperative side effects. For example, the fields of endoscopic-assisted surgery, microscopic surgery, and computer-enhanced instrumentation (e.g., the DaVinci System available from Intuitive Surgical, Inc. of Sunnyvale, Calif.) are generally concerned with minimally invasive surgery ("MIS") procedures and techniques, which have proven to be increasingly popular. Such popularity is at least partly due not only to the minimally-sized scars left by such techniques, but also to the minimal trauma to the fascia and muscle layers and the correspondingly faster recoveries this allows. However, surgeons must balance such considerations with providing adequate access to perform various surgical procedures. A typical surgical procedure involves a cutting or dissecting phase and a closing phase. In recent years, considerable progress has been made in minimizing surgical cutting, dissecting and shaping. Surgical closing techniques involve sutures, clips, staples and adhesives. However, suturing can be time-consuming and tedious. Moreover, the tissue structures to be joined may not be amenable to other closure techniques. MIS often restricts access to the separated tissue structures, thus making it more difficult to approximate and close same.

In contrast to MIS, some surgical procedures, by their nature, must include long incisions. Examples include cutaneous excisional procedures such as "lifts" and reduction procedures, flap procedures for closure of defects, and many bariatric procedures. Suturing in these extensive defects can be time-consuming and tedious.

The "first intention" (primary intention healing) in surgery is to "close" the incision. For load-bearing tissues, such as bone, fascia, and muscle, this requires substantial material, be it suture material, staples, or plates and screws. For the wound to be "closed," the epithelial layer must seal. To accomplish this, the "load bearing" areas of the cutaneous and subcutaneous layers (i.e., the deep dermal elastic layer and the superficial fascia or fibrous layers of the adipose tissue, respectively) must also at least be held in approximation. Important considerations include controlling infection and bleeding, reducing scarring, eliminating the potential of hematoma, seroma, and "dead-space" formation and managing pain. Dead space problems are more apt to occur in the subcutaneous closure. Relatively shallow incisions can normally be closed with surface-applied closure techniques, such as sutures, staples, glues, and adhesive tape strips. However, deeper incisions may well require not only skin surface closure, but also time-consuming placement of multiple layers of sutures in the load-bearing planes. Absorbable sutures are commonly used for this purpose and comprise an important class of surgical sutures. Depending on various factors, absorbable sutures typically dissolve over a period of a few days to a few months. Commercially available examples include Monocryl® monofilament absorbable synthetic sutures comprising a poliglecaprone and PDS® (polydrioxanone) and Vicryl® (polyglactin) sutures, all available from Ethicon, Inc., of Somerville, N.J.

Surgical mesh is commonly used to span or reinforce load-bearing planes or defects in them. When coupled with sutures or fasteners, surgical mesh represents another important class of surgical closure devices. Applications include reconstruction, hernia repair, and organ repair. In such procedures, surgical mesh fabric prostheses are inserted into patients through either open surgery or endoscopic (MIS) procedures. Knitted surgical mesh for hernia repair is disclosed in the Agarwal et al. U.S. Pat. No. 6,287,316, which is assigned to Ethicon, Inc. Another Ethicon, Inc. patent, Duncan U.S. Pat. No. 4,548,202, discloses mesh tissue fasteners including various fastening members with spaced-apart legs for passing through tissue portions. Another closure procedure involves the placement of pins or rods through skin edge or bone followed by the placement of an external clamp or fixator device spanning the wound and frequently incorporating a worm-screw apparatus capable of progressive tightening over time to effect closure, stabilization or distraction.

Fluid management represents another important aspect of both open and minimally invasive surgery. Postoperative fluid drainage can be accomplished with various combinations of tubes, sponges, and porous materials adapted for gathering and draining bodily fluids. The prior art includes technologies and methodologies for assisting drainage. For example, the Zamierowski U.S. Pat. Nos. 4,969,880; 5,100,396; 5,261,893; 5,527,293; and 6,071,267 disclose the use of pressure gradients, i.e., vacuum and positive pressure, to assist with fluid drainage from wounds, including surgical incision sites. Such pressure gradients can be established by applying porous foam material either internally or externally to a wound, covering same with a permeable, semi-permeable, or impervious membrane, and connecting a suction vacuum source thereto. Fluid drawn from the patient is collected for disposal. Such fluid control methodologies have been shown to achieve significant improvements in patient healing. Another aspect of fluid management, postoperative and otherwise, relates to the application of fluids to wound sites for purposes of irrigation, infection control, pain control, growth factor application, etc. Wound drainage devices are also used to achieve fixation and immobility of the tissues, thus aiding healing and closure. This can be accomplished by both internal closed wound drainage and external vacuum devices. Fixation of tissues in apposition can also be achieved by bolus tie-over dressings (Stent dressings), taping, strapping and (contact) casting.

Heretofore, there has not been available a flexible medical closure screen and method with the advantages and features of the present invention, including the combination of same with negative pressure wound therapy ("NPWT").

SUMMARY OF THE INVENTION

In the practice of one aspect of the present invention, a medical closure screen device is provided, which includes a mesh screen comprising tubular vertical risers, barbed filaments therebetween and horizontal spacers. Integral or separate sutures can be provided. An optional perimeter member partly surrounds the screen member and can comprise a perimeter tube fluidically coupled with the vertical risers to form a tubing assembly. The tubing assembly cooperates with the vertical risers to extract fluid from the tissue separation in a drain mode and to introduce fluid thereinto in an irrigate mode. In one embodiment of the invention the tubing assembly is fluidically coupled to a vacuum source to facilitate drainage. In another embodiment of the invention, the perimeter tube is passed through the surrounding tissue to secure the screen member in place. Fluid transfer elements, such as sponges, foams, absorbent mesh, microtubular materials and the like, are optionally placed adjacent to and over an extension of the screen for fluid transfer, for example, in conjunction with a vacuum or pump source. Another embodiment of the invention includes a suture connected to the screen and adapted for securing same in a tissue separation.

Alternative embodiment vertical risers are also disclosed, and can provide active fluid transfer utilizing the patient's body dynamics. Yet another alternative embodiment of the present invention utilizes the screen barbs for mechanical fixation in a separation for closure of same. Separation closure, irrigation and drainage methodologies are disclosed utilizing various combinations of closure screens, tubing, sutures, fluid transfer elements and gradient force sources. The closure screen of the present invention uses mechanical and other forces associated with screens and barbed strands for securing separated tissues together and for eliminating or reducing the formation of subcutaneous voids or pockets, which can potentially form hematoma and seroma effects. Further embodiments of the invention include flexible medical closure screens and circumferential medical closure devices, and methods of closing separated tissue with same.

BRIEF DESCRIPTION OF THE DRAWINGS

FIG. 1 is a side elevational view of a medical closure screen device embodying the present invention.

FIGS. 5a-e show a tissue separation closure procedure embodying the method of the present invention.

FIG. 6a is an enlarged, fragmentary, cross-sectional view of the closure screen in a tissue separation, with skin hooks shown in hidden lines for positioning the separated tissue portions along the closure screen.

FIG. 6b is an enlarged, fragmentary, cross-sectional view of the closure screen in a substantially closed tissue separation.

FIGS. 7a-f show a tissue separation closure procedure embodying the method of the present invention and utilizing optional sponge or foam fluid transfer elements and a tubing placement tool.

FIG. 9 shows a needle mounting a length of drain tubing and adapted for passing same through tissue.

FIG. 11a is an enlarged, fragmentary, side elevational view thereof, taken generally within circle 11a in FIG. 10.

FIG. 11b is an enlarged, fragmentary, side elevational view thereof, showing modified vertical risers.

FIGS. 14a-g show a tissue separation closure procedure utilizing the screen-only embodiment of the closure screen.

FIG. 15a is a side elevational view of a modified vertical riser with flexible, multi-tube risers forming a fluid passage.

FIG. 15b is a cross-sectional view thereof, taken generally along line 15b-15b in FIG. 15a.

FIG. 16a is a fragmentary, side elevational view thereof, shown in a compressed configuration.

FIG. 16b is a cross-sectional view thereof, taken generally along line 16b-16b in FIG. 16a.

FIG. 17 is a cross-sectional view of another modified vertical riser construction with risers bundled in a different configuration, with barbs.

FIG. 21 is an enlarged, cross-sectional view of a closure screen comprising an alternative embodiment of the present invention, with barbs formed by cutting off the ends of looped filaments.

FIG. 22 is an enlarged, cross-sectional view of a closure screen comprising an alternative embodiment of the present invention, with barbs forming hooks and constructed by cutting looped filaments.

FIG. 23 is an enlarged, cross-sectional view of a closure screen comprising yet another alternative embodiment of the present invention, with barbs formed by cutting off the ends of looped filaments, which are laid over in a common direction or orientation.

FIG. 24 is an enlarged, cross-sectional view of a closure screen comprising a further alternative embodiment of the present invention, with barbs forming hooks and constructed by cutting looped filaments, which are laid over in a common direction or orientation.

FIG. 25 is a perspective view of another alternative embodiment of a one-sided closure screen system, which includes barbed strands forming prongs projecting from one side of the closure screen.

FIG. 26 is a fragmentary, side elevational view thereof.

FIG. 27 is an enlarged, perspective view thereof, particularly showing the prongs.

FIG. 31 is a fragmentary, side elevational view of an inside/outside barbed strand system closing a blood vessel.

FIG. 31a is a fragmentary, side elevational view of another inside/outside barbed strand system closing a blood vessel.

FIG. 32 is a fragmentary, side elevational view of another inside/outside barbed strand system closing a blood vessel.

FIGS. 33-35 are side elevational views of another alternative embodiment of a circumferential closure device, shown connecting an elongated tissue.

FIG. 36 is an enlarged, fragmentary detail of one construction option for any strand of the circumferential closure device, taken generally within circle 36 in FIG. 33.

FIG. 36a is an enlarged, fragmentary detail of another alternative embodiment of a circumferential closure device, with an auxiliary strand adapted for repositioning and reorienting the prongs.

FIG. 37 is a perspective view of another alternative embodiment circumferential closure device, with internal prongs.

FIG. 38 is a perspective view of another alternative embodiment circumferential closure device, with internal, annular tissue-engaging ridges.

FIG. 39 is an enlarged, cross-sectional view of the circumferential closure device, taken generally along line 39-39 in FIG. 38.

DETAILED DESCRIPTION OF THE PREFERRED EMBODIMENTS

I. Introduction and Environment

Figure 3:
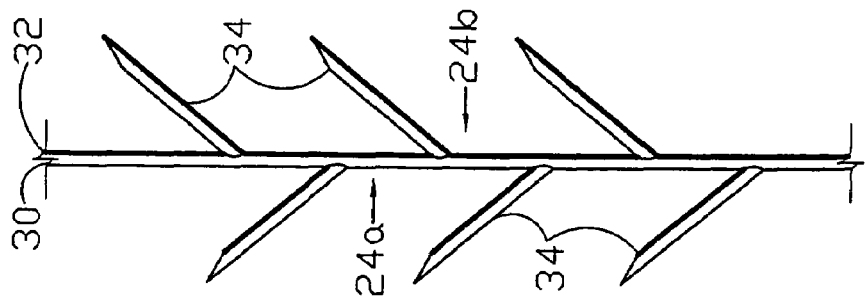
FIG. 3 is an enlarged, fragmentary, side elevational view thereof, taken generally along line 3-3 in FIG. 2, and particularly showing a barbed strand.
Figure 2:
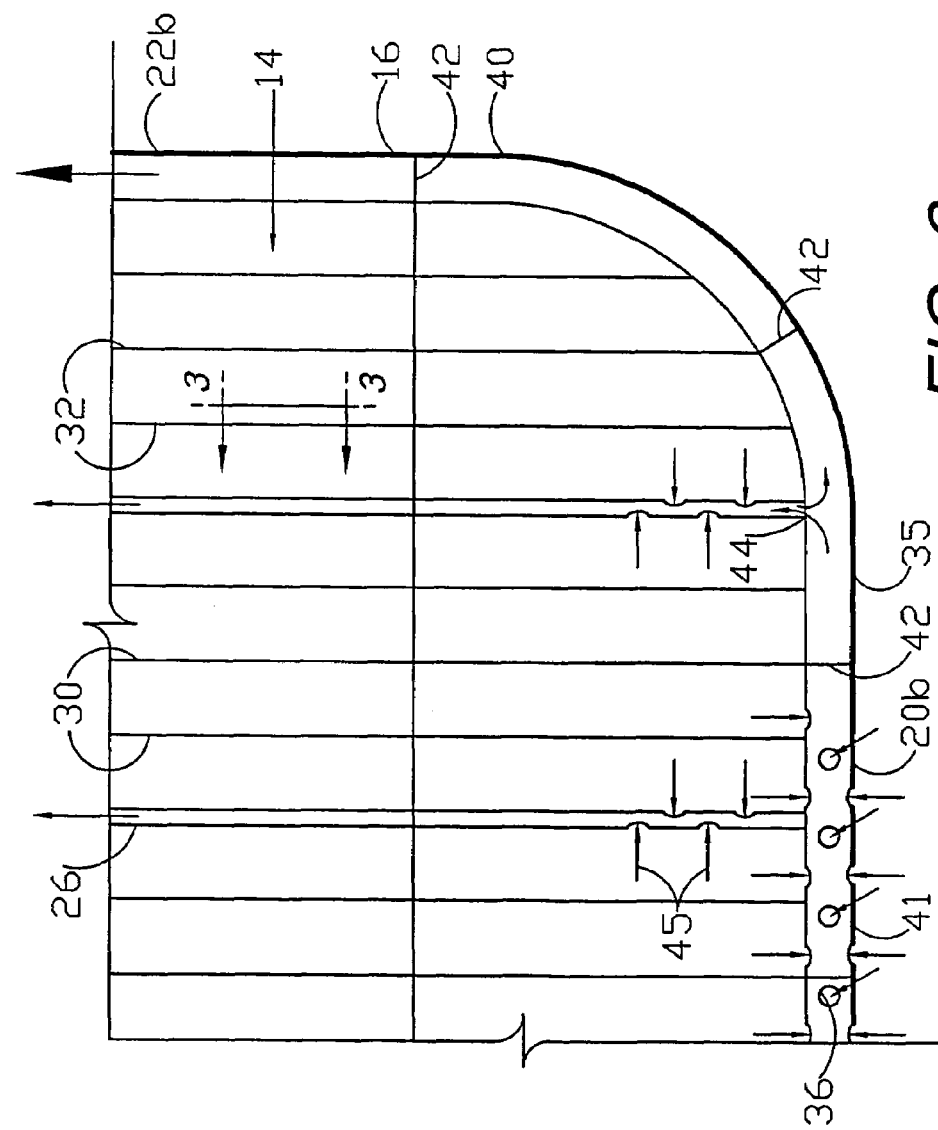
FIG. 2 is an enlarged, fragmentary, side elevational view thereof, taken generally within circle 2 in FIG. 1.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. The words "horizontal" and "vertical" generally mean side-to-side and top-to-bottom, respectively. Said terminology will include the words specifically mentioned, derivatives thereof and words of a similar import.

Referring to the drawings in more detail, the reference numeral 2 generally designates a medical closure screen device or system embodying the present invention. Without limitation on the generality of useful applications of the closure screen system 2, the primary application disclosed herein is for assistance with the closing, draining, irrigating and healing of a separation of first and second tissue portions, such as a wound or incision 4. As shown in FIG. 5a, the wound 4 extends from and is open at the dermis 6, through the deep dermal layer 7 and the subcutaneous layer 8, and to approximately the fascia 10. The wound 4 displays edges 12a,b, which correspond to first and second tissue portions. The closure screen device 2 generally comprises a screen 14, a screen perimeter member 16 and an input/output (I/O) subsystem 18.

II. Screen 14

The screen 14 includes upper and lower margins 20a,b; first and second ends 22a,b; and first and second faces 24a,b. The screen 14 generally forms a grid configuration with vertical, hollow, perforated tubular risers 26 cross-connected by horizontal spacer members 28. Multiple barbed strands 30 are positioned between the risers 26. The risers 26, the spacers 28 and the strands 30 are preferably joined at their respective intersections. As shown in FIG. 3, each strand 30 includes a filament 32 with multiple, pointed barbs 34 extending upwardly and outwardly on both sides in staggered, spaced relation. The barbs 34 generally project outwardly from the screen faces 24a,b, for purposes which will be described in more detail hereinafter.

The screen or mesh 14 material can be either dissolvable (absorbable) or non-dissolvable (non-absorbable) and can be chosen from a number of commercially-available, biocompatible products, which are commonly used in medical applications for sutures, implantable meshes, and similar medical devices.

Examples of absorbable materials include, but are not limited to: aliphatic polyesters, which include, but are not limited to: homo polymers and copolymers of lactide, .epsilon.-caprolactone, p-dioxanone, trimethylene carbonate, alkyl derivatives of trimethylene carbonate, .delta.-hydroxyvalerate, 1,4-dioxepan-2-one, 1,5-dioxepan-2-one, 6,6-dimethyl-1,4-dioxan-2-one and polymer blends thereof. Examples of nonabsorbable materials include, but are not limited to: cotton, linen, silk, polyamides, polyesters, fluoropolymers, polyolefins, polyethylene, metals and combinations thereof.

III. Screen Perimeter Member 16

The optional screen perimeter member 16 can comprise, for example, a flexible, perforated, hollow tube 35 with multiple orifices 36. As shown in FIG. 1, the tube 35 includes first and second legs 38, 40 extending generally along the screen first and second ends 22a,b, and a base leg 41 extending generally along the screen lower margin 20b. The tubing first and second legs 38, 40 terminate in respective first and second ends 38a, 40a. The tube 35 can be secured to the screen 14 by multiple ties 42, which can comprise extensions of the horizontal spacer members 28 and the strands 30. By providing dissolvable ties 42, the tube 35 can be designed for separation from the remainder of the closure screen 2 after a relatively short period of time. For example, the dissolvable material can dissolve into the patient's body after a few days, whereafter the tube 35 can be removed.

Optionally, portions of the tube 35 can be cut away from the screen 14. For example, the screen 14 can be separated along each screen end 22a,b, or it can be separated completely from the tube 35. In this manner the screen 14 and the tube 35 can be configured to accommodate a variety of conditions and tissue separation configurations.

The vertical risers 26 are optionally fluidically coupled to the tube 35 at respective T intersections 44. In this configuration the tube 35 and the vertical risers 26 cooperate to provide a manifold for fluid handling, i.e. either extraction or irrigation, as indicated by the fluid flow arrows 45.

IV. Input/Output (I/O) Subsystem 18

The input/output subsystem 18 is designed for extraction and/or irrigation of the patient's bodily fluids and/or external fluids. As shown in FIG. 1, the input/output subsystem 18 includes first and second I/O devices 18a,b attached to the tubing first and second leg ends 38a,b, which in this configuration are considered the "port" ends of the tube 35. One or both of the I/O devices 18a,b can comprise a pressure differential source, such as the NPWT device, The V.A.C.® System™, available from Kinetic Concepts, Inc. of San Antonio, Tex. The use of such units for wound treatment and fluid management is disclosed in the Zamierowski U.S. Pat. Nos. 4,969,880; 5,100,396; 5,261,893; 5,527,293; and 6,071,267, which are incorporated herein by reference.

Figure 4A:
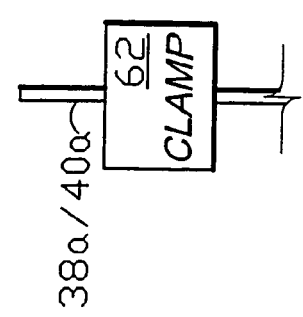
FIGS. 4a-f show alternative perimeter tube end closures comprising: 4a) subdermal termination; 4b) knotted end; 4c) Leur lock; 4d) transfer element (i.e., sponge); 4e) vacuum source; and 4f) clamped end.
Figure 4B:
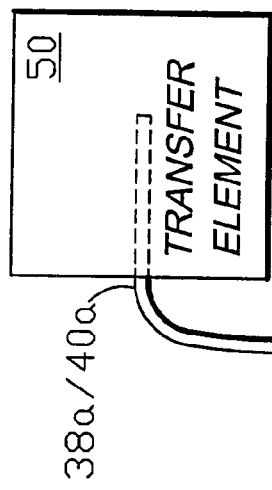
Figure 4C:
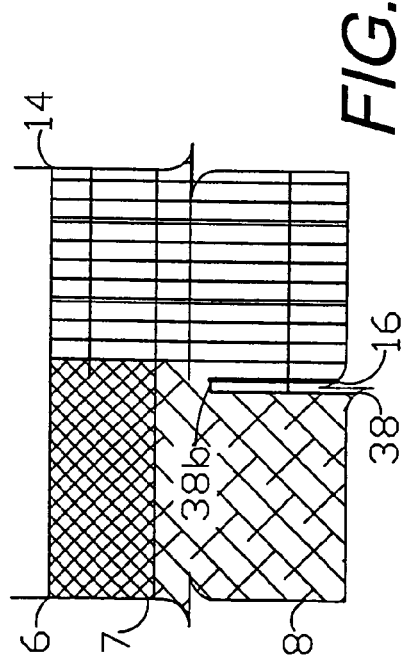
Figure 4F:
Figure 4D:
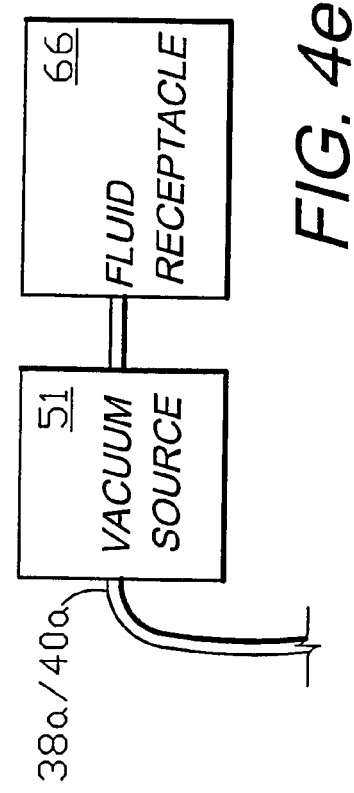
Figure 4E:
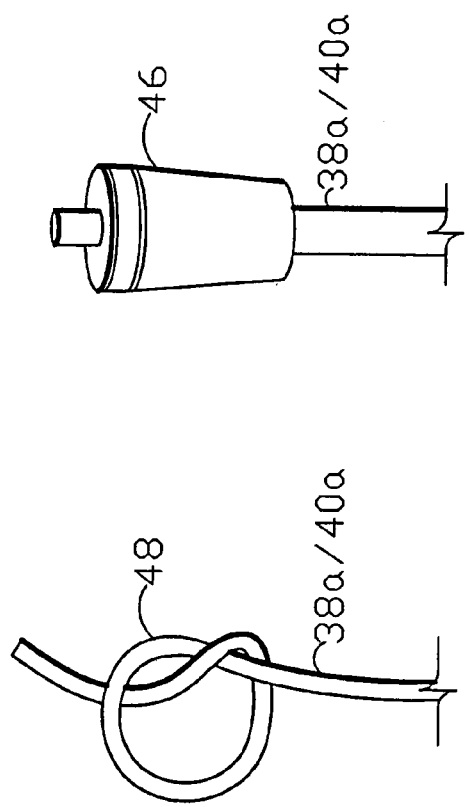

Alternatively, the tubing port ends 38a,b can be connected to various other sources of pressure differential and various drainage and irrigation devices. For example, they can be cut short below the dermis 6 and left within the separation 4 for sealing by the adjacent tissue portions 12a,b. FIG. 4a shows a truncated tubing end 38b. The tubing ends 38a/40a can be knotted (as shown at 48 in FIG. 4b), clipped, tied (e.g., with a suture) or otherwise closed off either above or below the dermis 6. FIG. 4c shows a Leur lock coupling 46 mounted on a tubing end 38a/40a. Still further, a transfer element comprising a piece of foam or sponge 50 can be coupled to the tube 35 at an end 38a/40a (FIG. 4d). Examples of such foam and sponge materials and configurations are discussed in the Zamierowski U.S. patents identified above. A pressure differential source, such as a vacuum source 51, can be connected to a tube end 38a/40a and to a fluid receptacle 66, as shown in FIG. 4e. A clamp 62 is shown in FIG. 4f and closes the tube end 38a/40a. The clamp 62 can be chosen from among several suitable clamps, which are commonly used for medical applications.

Either tube end 38a/40a can function as either an inlet port or an outlet port with respect to the system 2. For example, suction can be applied for pulling fluid from the patient through the system 2 through either tube end 38a/40a. Still further, fluid can be pulled in both directions through the system 2 by alternately or jointly applying suction to the tube ends 38a/40a. For example, suction can be simultaneously applied to both tube ends 38a/40a.

V. Operation And Closure Method

Figure 5B:
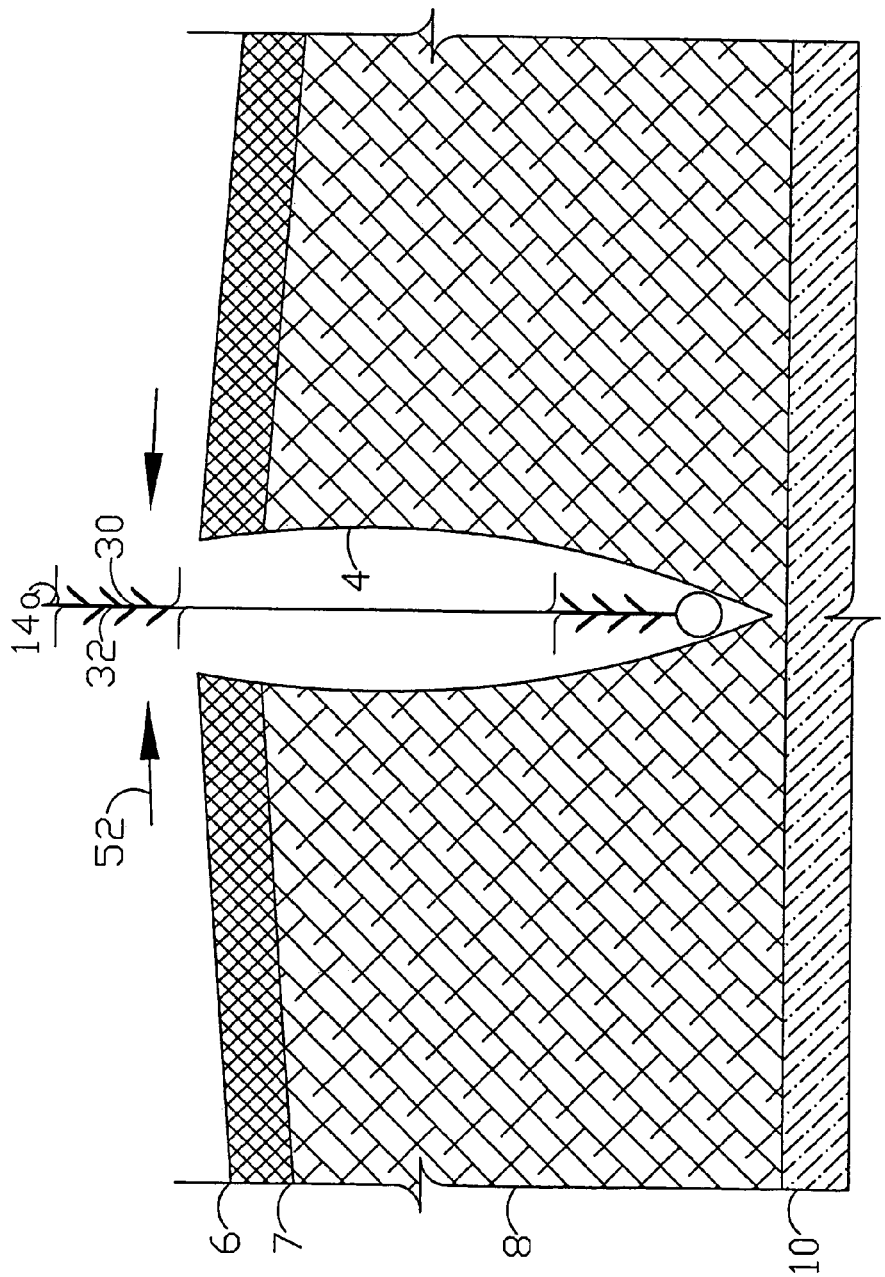
Figure 5C:
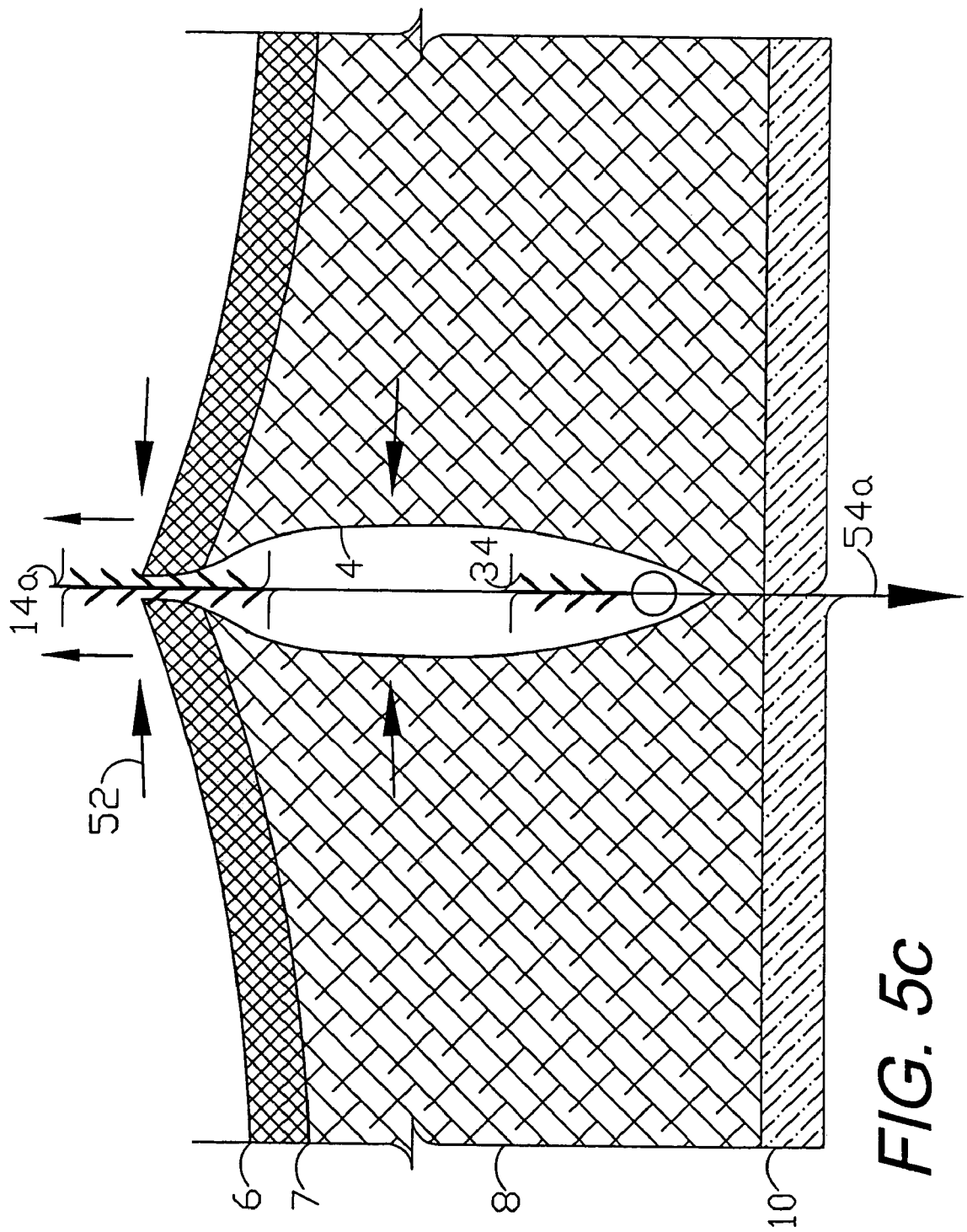
Figure 5D:
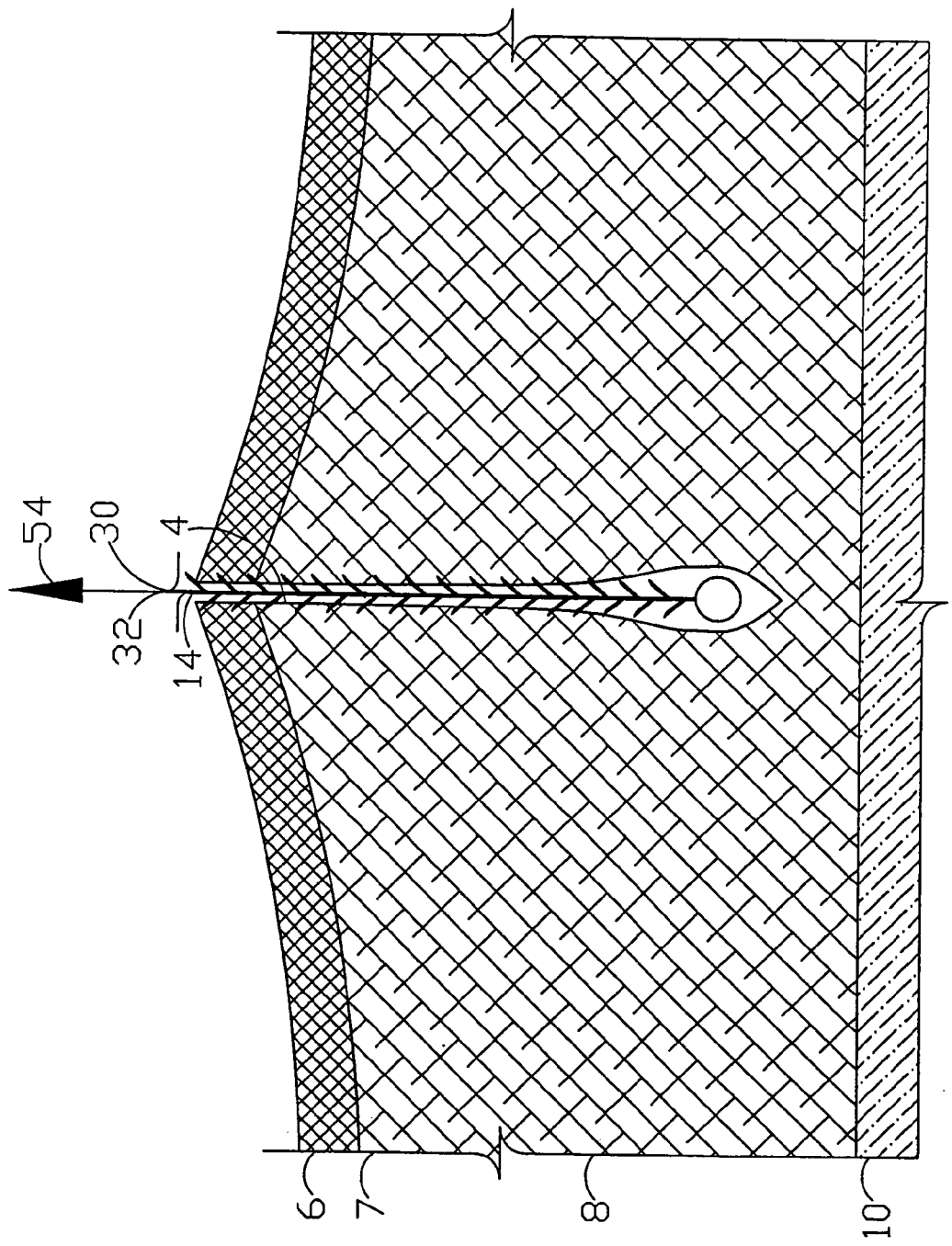

FIGS. 5a-e show an installation methodology utilizing the system 2 of the present invention. In FIG. 5a, the closure screen 2 is placed in the separation 4 with the tubing base 41 located at the bottom of the separation (e.g., wound or incision) 4 and in proximity to the fascia layer 10. As shown, the tissue portions or wound/incision edges 12a,b are spaced apart. The screen upper margin 20a can protrude outwardly from the dermis 6. FIG. 5b shows the tissue separation edges 12 being pushed together as indicated by the force arrows 52. FIG. 5c shows the separation edges 12 engaged at the dermis 6, and spaced apart somewhat within the subcutaneous layer 8. The edges 12 can be pushed together as indicated by the force arrows 52. Moreover, the screen 2 can be held or positioned inwardly in order to advance the barbs 34 in the separation edges 12, as indicated by the inward or downward force arrows 54a. FIG. 5d shows the separation edges 12a,b substantially closed on the screen 2. Tugging on the screen 14 in the general direction of the outward force arrow 54b sets the mesh barbs 34.

Figure 5E:
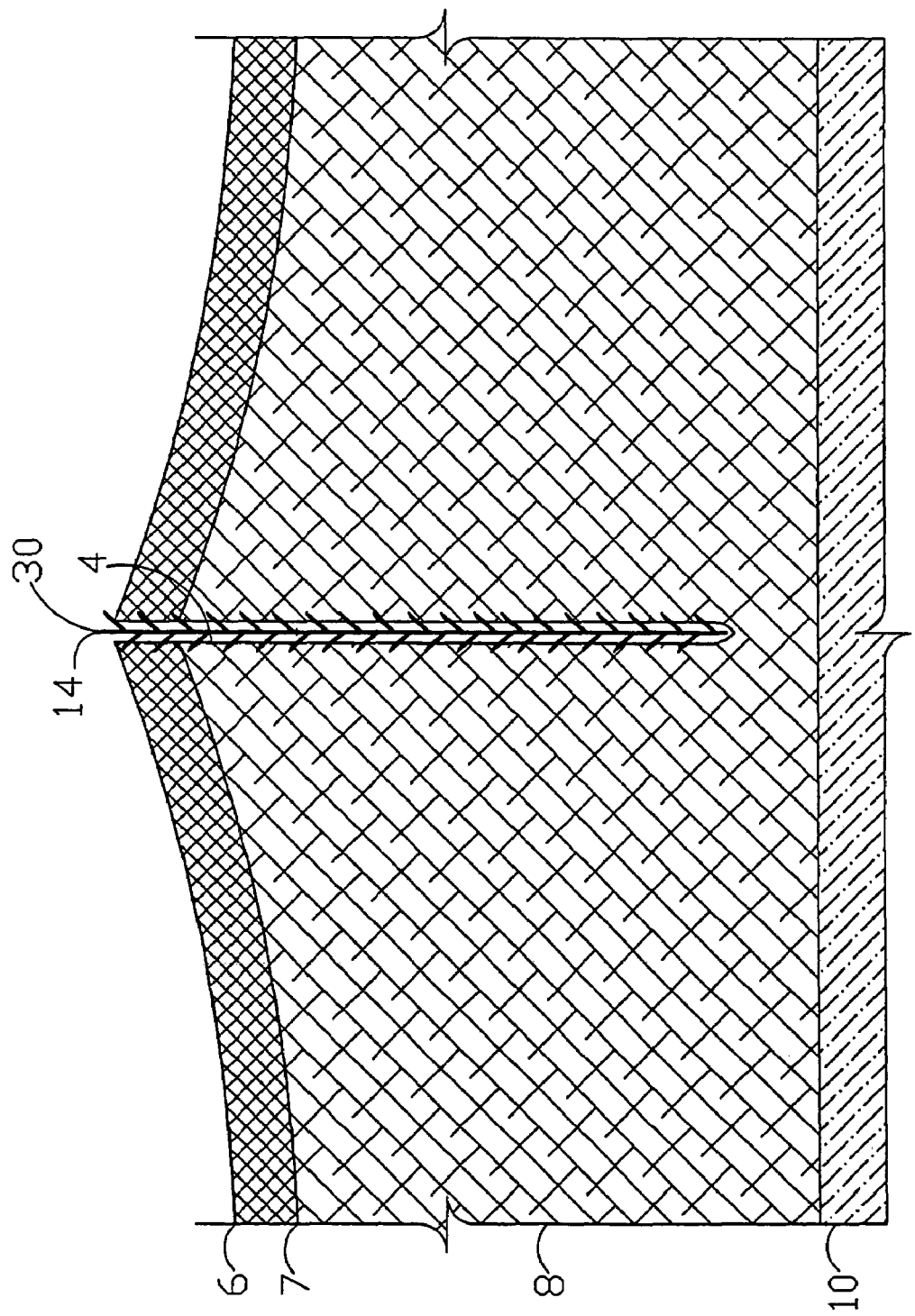

FIG. 5e shows the separation 4 closed on the closure screen 2, with the tubing 35 removed from the screen 14. The tubing 35 can be removed either pre-installation by cutting the ties 42, or post-installation by allowing the ties 42 to dissolve, whereafter the unsecured tubing 35 can be extracted.

FIG. 6a shows the barbs 34 compressed by engagement with the separation edges 12a,b. As shown, the separation edges 12 can be manually closed by pressing along the horizontal force arrows 52. The barbs 34 allow the separation edges 12a,b to slide upwardly or outwardly along the screen 14. This process can be repeated until the separation 4 is closed, as shown in FIG. 6b. Any protruding length of the screen 14 can be cut close to the dermis 6. In the final configuration (FIGS. 5e and 6b), the barbs 34 are embedded in the tissue adjacent to the separation edges 12a,b and thus secure the separation 4 in a closed position. The fluid conducting properties of the screen 14 facilitate extracting fluid. An outward or upward force arrow 54b indicates a force direction whereby the screen barbs 34 are set in the adjoining tissue. It will be appreciated that the screen 14 can be securely set in place with the barbs 34, yet the separation edges 12a,b will remain capable of sliding up on the screen 14 by disengaging the barbs 34 with lateral forces, as shown in FIG. 6a. Skin hooks 55 can be used for engaging the tissue portions 12a,b and tugging same outwardly as shown in FIG. 6a. The skin hooks 55 can facilitate positioning and repositioning the screen 14.

VI. Alternative Embodiment Closure Screen Systems and Methodologies

Figure 7A:
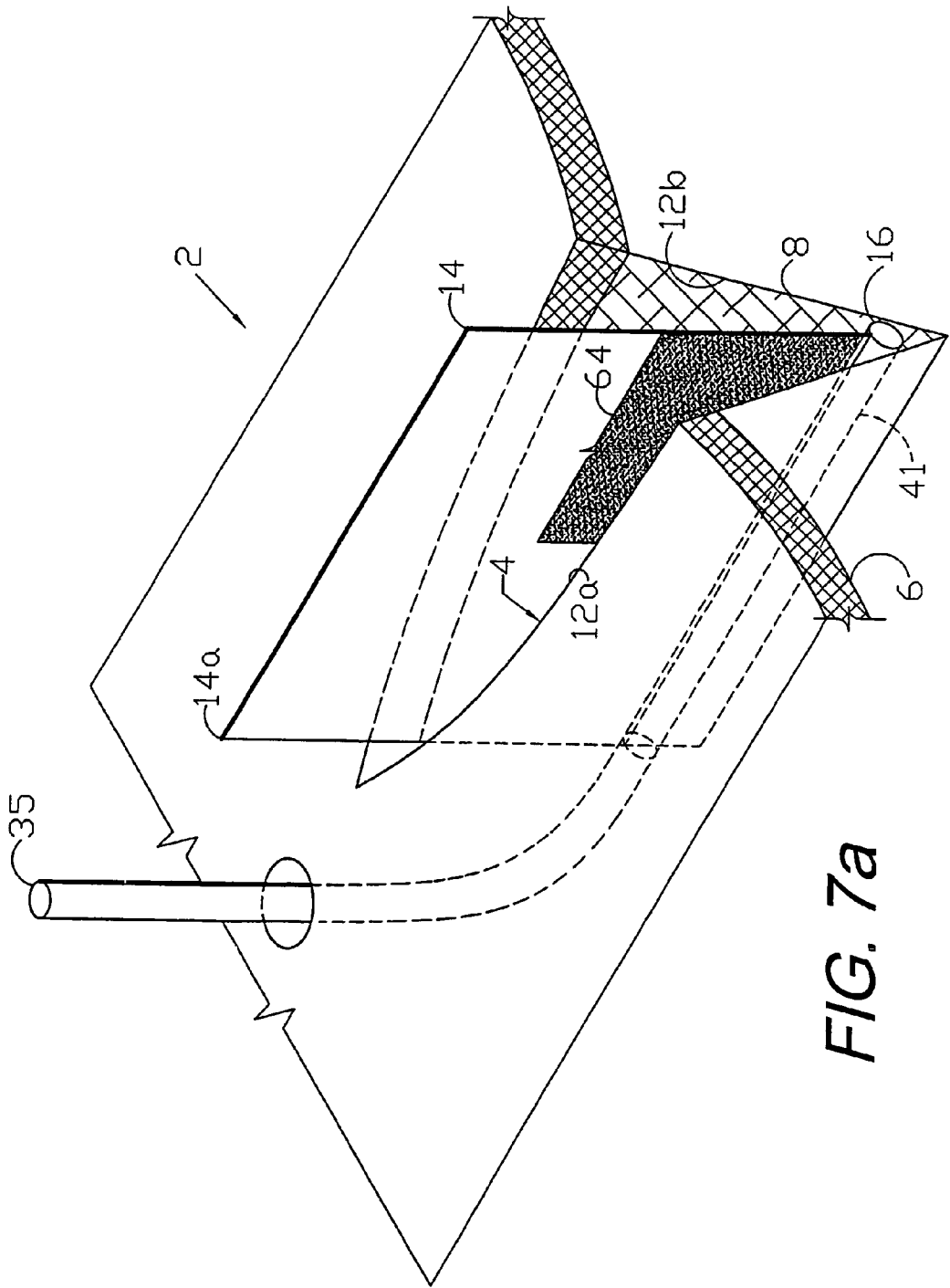
Figure 7B:
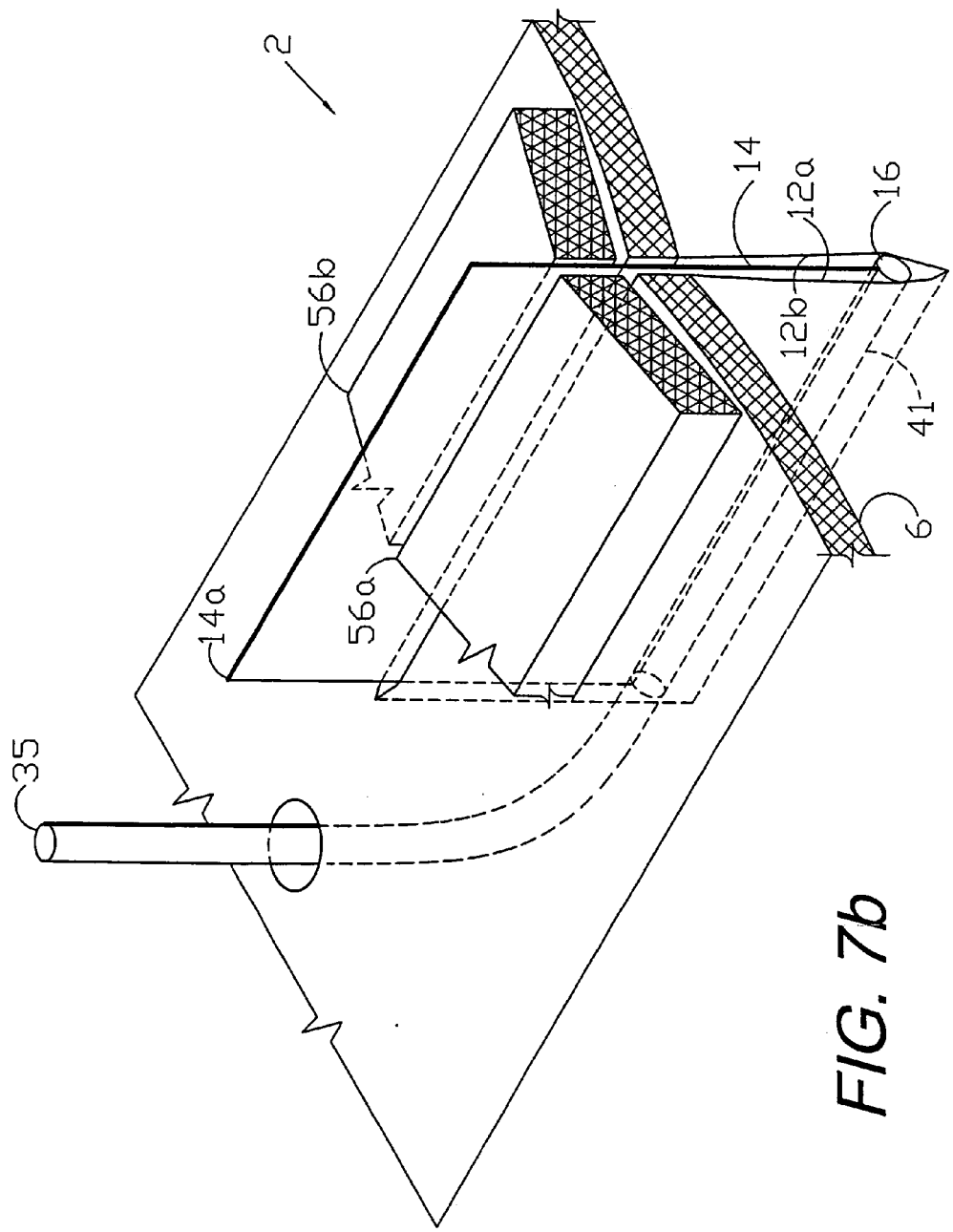

FIGS. 7a-f show an alternative procedure for mounting the closure screen 2 in a wound drainage application utilizing pressure differential. As shown in FIG. 7a, the tubing 35 can pass through the tissue adjacent to the wound 4 and exit the dermis 6 for termination of the tubing end 38a/40a as described above. An optional layer of a suitable, biocompatible adhesive 64 is shown applied to the closure screen first face 24a for securing same to the first wound edge 12a. FIG. 7b shows the screen 14 extending upwardly from the dermis 6 with the wound edges 12a,b brought together in a manner similar to that described above.

Figure 7C:
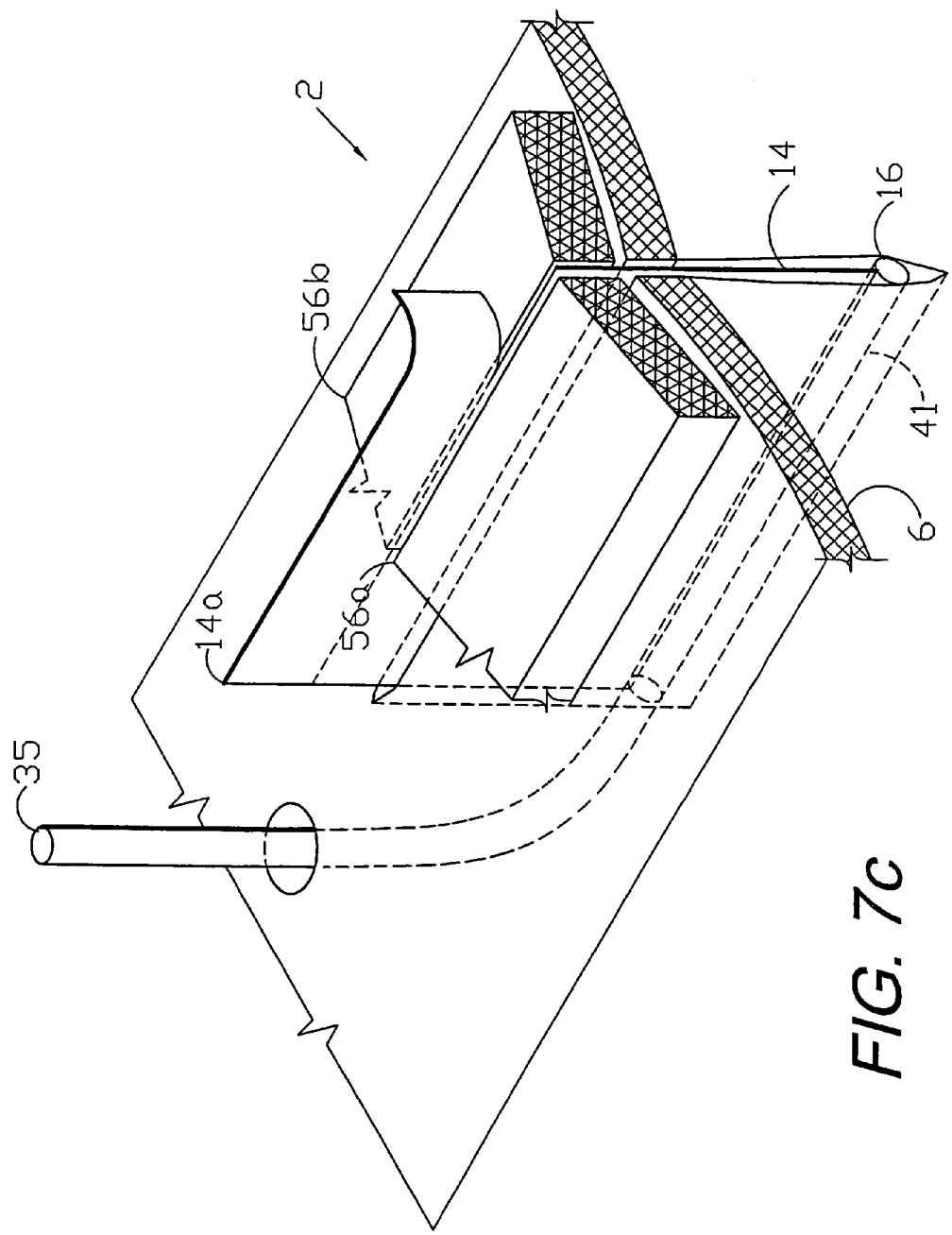
Figure 7D:
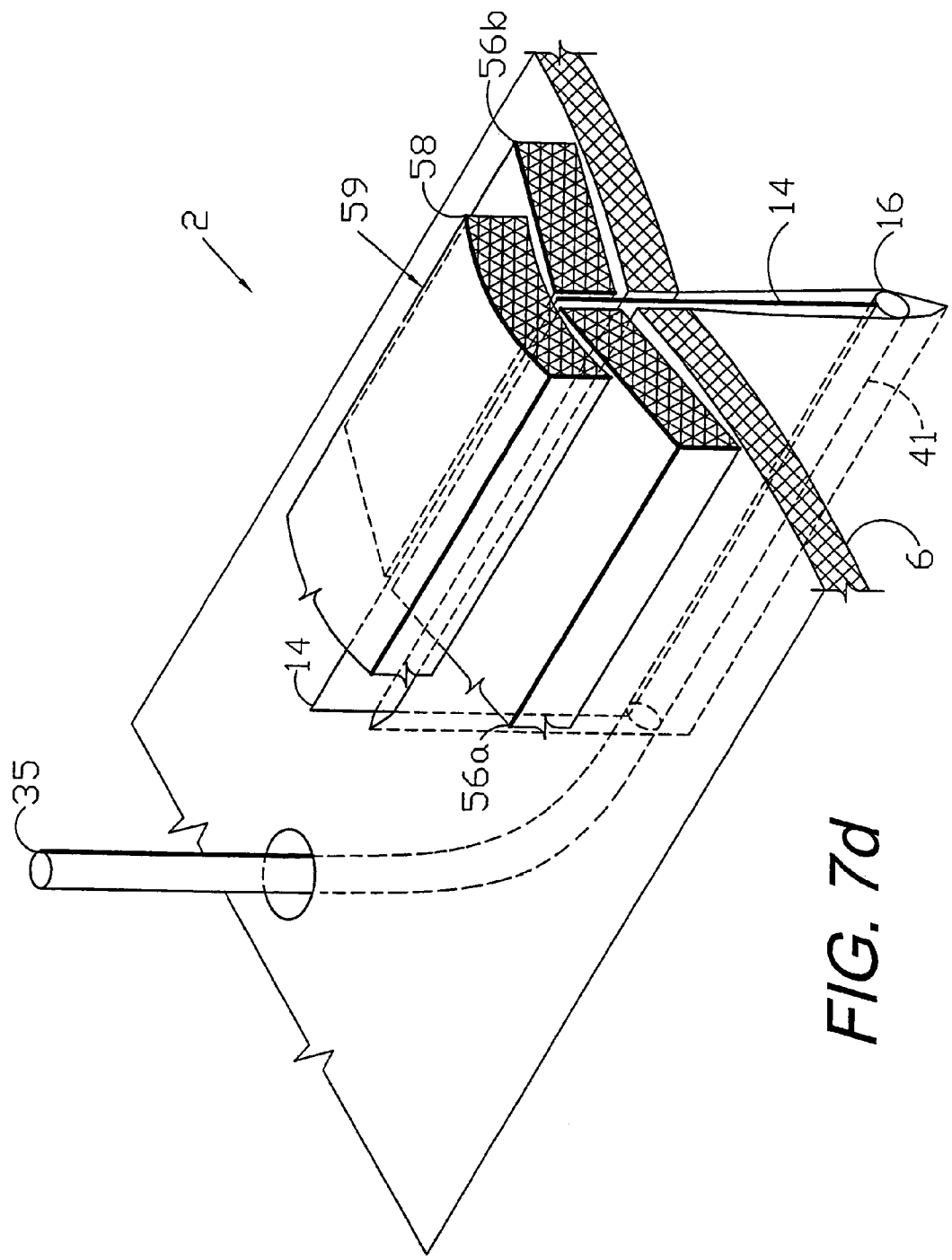

The input/output subsystem 18 includes a pair of optional fluid transfer elements comprising foam or sponge members 56a,b placed on the dermis 6 on either side of a protruding portion 14a of the screen 14. The screen 14 is then cut to a level generally flush with the upper surfaces of the sponges 56a,b, as shown in FIG. 7c. An optional sponge bridge 58 is placed over the sponge members 56a,b (FIG. 7d). Examples of suitable transfer element materials are discussed in the Zamierowski patents noted above and include open-cell, porous foam materials (e. g., polyurethane ester (PUE)) chosen for their hydrophobic properties and passage of liquids. Polyvinyl acetate (PVA) material can be used for its hydrophilic properties. The transfer element subassembly 59 formed by the sponge members 56a,b and 58 can be connected to a vacuum source, a fluid irrigation source, etc.

Moreover, it can be connected to additional fluid transfer elements and covered with various flexible membranes and drapes, which can be semi-permeable or impervious, as indicated for the closure and treatment of particular separations and wounds.

FIG. 7e shows a tubing placement tool 120 with a handle 122, a shaft 124 and a hook 126 terminating at a pointed or rounded, bullet-shaped tip 128. FIG. 7f shows the tool 120 passing tubing 35 through tissue in the subcutaneous layer 8 and into proximity with the dermis 6. The tip 128 is received in a blind end 134 of the tubing 35 through a notch 136 formed therein. The thrust of the tool 120 causes tenting of the dermis 6, as shown at 138, whereat the dermis 6 can be opened with a scalpel 140 and the tubing 35 can exit the patient for suitable termination arrangements, such as those shown in FIGS. 4a-f above.

Figure 8:
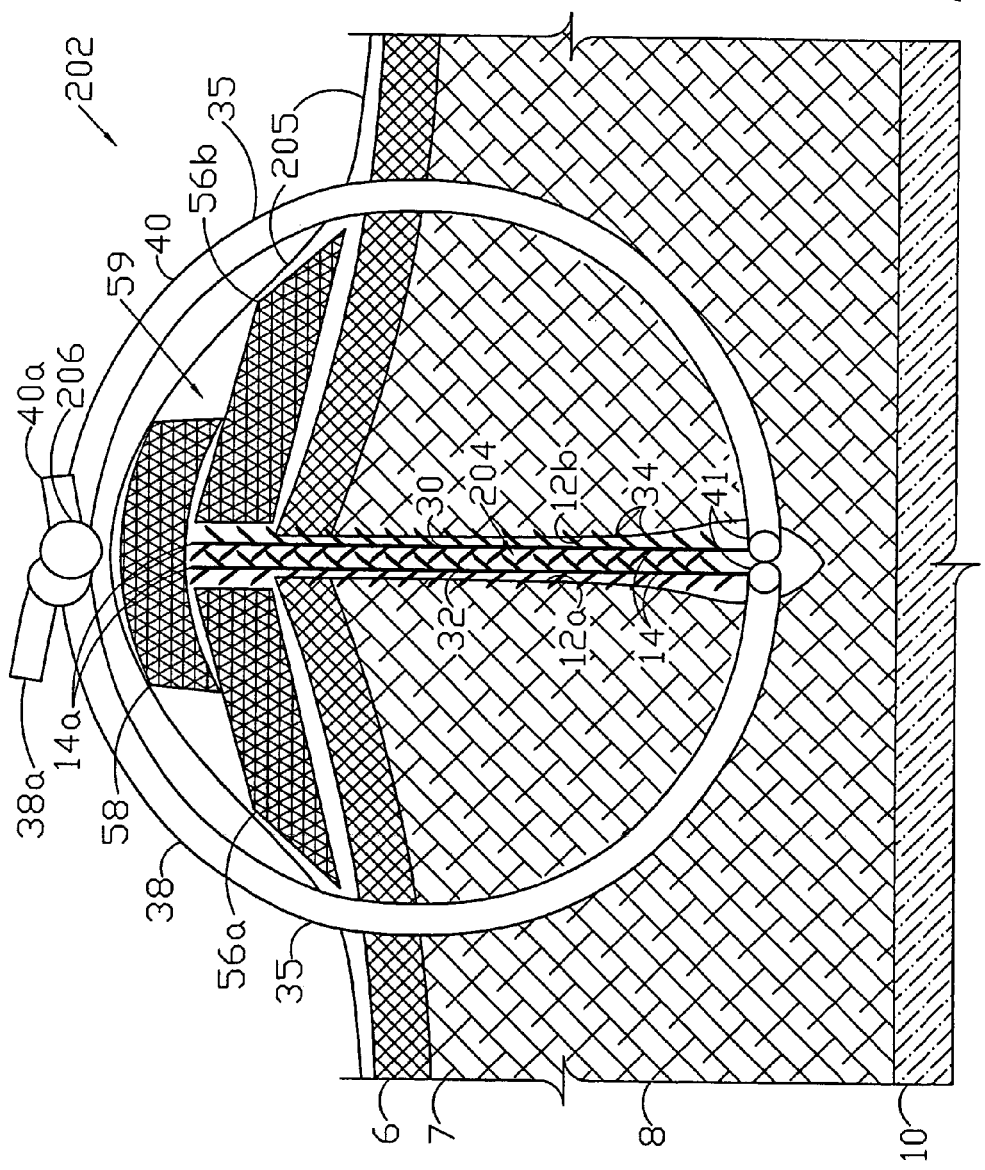
FIG. 8 is a cross-sectional view of a tissue separation closure utilizing tubing for securing the closure screen with a fluid transfer subassembly connected to an upper edge of the closure screen.

FIG. 8 shows a modified embodiment closure system 202 with a pair of screens 14 positioned generally end-to-end in a separation 204. A transfer element subassembly 59 is placed over the separation 204 and a membrane drape 205 is placed thereover. The tube 35 is passed through tissue on either side of the separation 204 (e.g., using the procedure and the tubing placement tool 120 described above) and exits the dermis 6 on either side of the transfer element subassembly 59. The tube 35 lengths are knotted at 206. The tube 35 lengths thus function as sutures or retainers for securing the closure system 202 in the separation 204. The tube ends 38a or 40a can be utilized for this purpose, thus leaving the other tubing ends available for fluid communication with one or more of the input/output subsystems 18 described above.

The tube 35 can be secured by suitable fasteners, such as clips and the like, located above the dermis 6. Moreover, the screens 14 can be overlapped, abutted, spaced slightly and otherwise configured and positioned as necessary for particular tissue separations. Still further, the screens 14 are adapted to be trimmed as necessary.

FIG. 9 shows a modified embodiment tubing/suture subassembly 220 with a Trocar instrument 222 including a sharpened, distal end 224 and a proximate end 226 with multiple, annular ridges 226a. A length of flexible tubing 228 combines the functions of screen perimeter member and suture. The flexible tubing 228 terminates at an end 228a adapted for releasably mounting on the needle proximate end 226, whereat it is retained in place by the ridges 226a. The tubing 228 is optionally connected to the screen 14 as described above and can include perforations 228b for fluid drainage and/or irrigation in conjunction with input/output subsystems 18, also as described above. The tubing/suture subassembly 220 is adapted for securing the screen 14 in place and for closing the separation 4 by passing the tubing 228 through adjacent tissue. The tubing/suture subassembly 220 and the screen 14 can be prepackaged and presterilized for closing and treating separations, which can include wounds and incisions.

Figure 10:
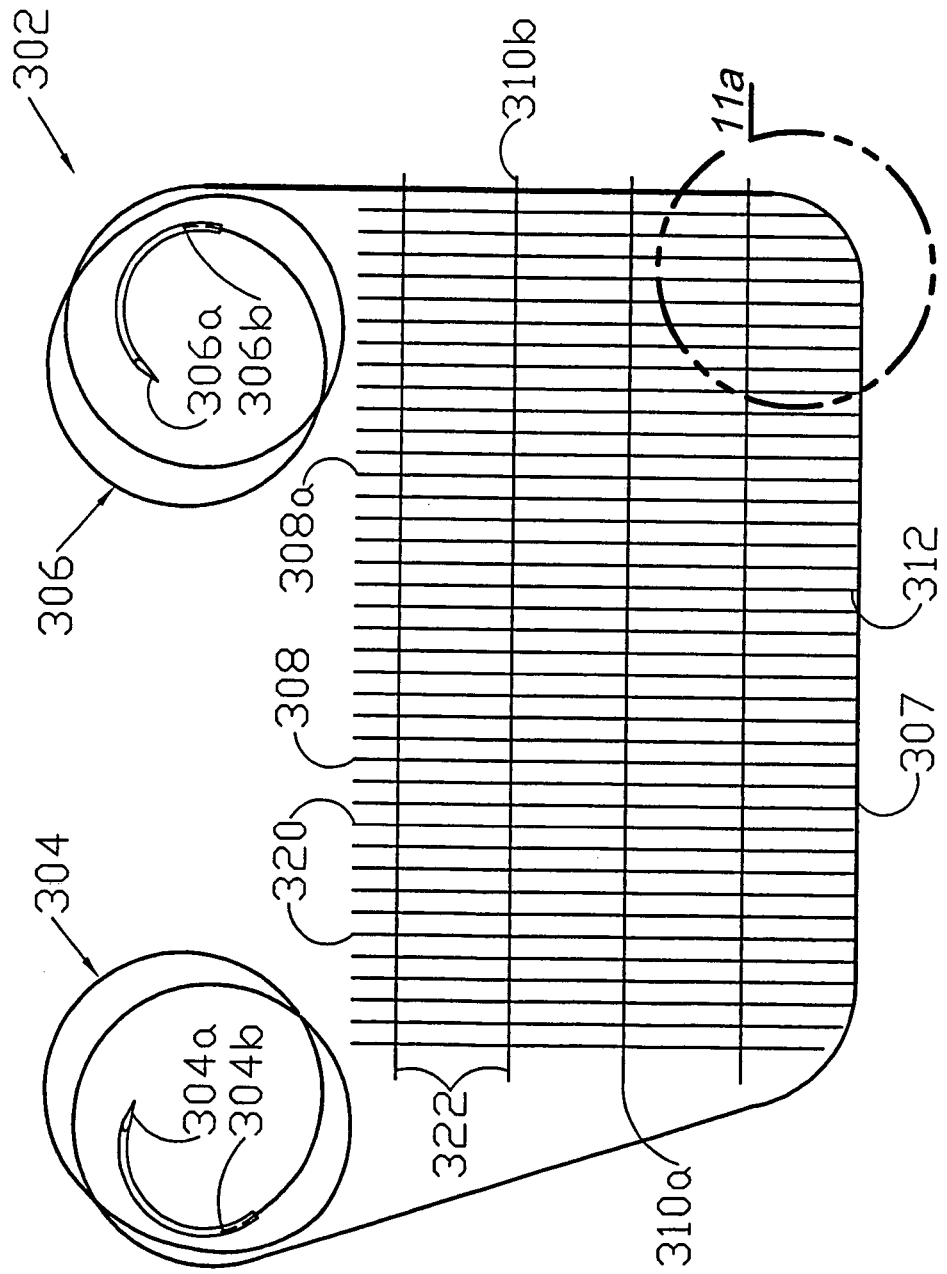
FIG. 10 is a side elevational view of a closure screen comprising an alternative embodiment of the present invention, with a perimeter suture.

FIGS. 10, 11a and 11b show modified embodiment closure screen systems 302 with first and second suture subassemblies 304, 306 comprising the screen perimeter member. The suture subassemblies 304, 306 include respective curved needles 304a, 306a which are swaged or adhesively connected to opposite ends 304b, 306b of a common length of suture thread 307. The suture thread 307 can be absorbable or nonabsorbable. As shown in FIG. 10, the screen closure system 302 can be preassembled with the suture thread length 307 releasably secured to the perimeter 308a of a screen 308. Prior to installation of the screen 308, the suture 307 can be disconnected or severed therefrom, either partly or completely. For example, the suture 307 can be separated along the screen ends 310a, 310b respectively, thereby leaving the suture thread lengths secured only along a screen lower margin 312.

In operation, the suture subassemblies 304, 306 facilitate installation of the suture/screen closure system 302, thereby providing a preassembled device which incorporates the necessary components for securing same in a separation 4. For example, the screen 308 can be secured at the bottom alone by passing the suture subassemblies 304, 306 through tissue portions located at the bottom of the separation 4. Alternatively, the suture subassemblies 304, 306 can be passed through the adjacent tissue and exit the surface of the dermis 6, whereby the suture subassemblies 304, 306 can be used for closing the separation 4 at the dermis 6. Barbed strands 320 can interact with the tissue portions 12a,b as described above, whereby the screen 308 provides a relatively secure mechanical connection between the separated tissue portions 12a,b. The suture subassemblies 304, 306 can be utilized for various purposes in the separation 4, including attachment and tacking of the dermis 6, the deep dermal layer 7, the subcutaneous layer 8 and the fascia 10. Still further, all or part of the suture subassemblies 304, 306 can be removed, and additional suture subassemblies can be mounted on or sutured to the screen 308.

FIG. 11a shows the screen 308 attached to the suture thread 307. FIG. 11b shows an alternative construction screen 318 with hollow tubular vertical risers 324 located between adjacent, respective vertical strands 320, all connected by the spacers 322 and adapted for communicating fluid with the separation 4 through the open riser ends 324a and the perforations 324b, as indicated by the fluid flow arrows 326. All or part of the screen/suture system 302 can comprise absorbable material.

Figure 12:
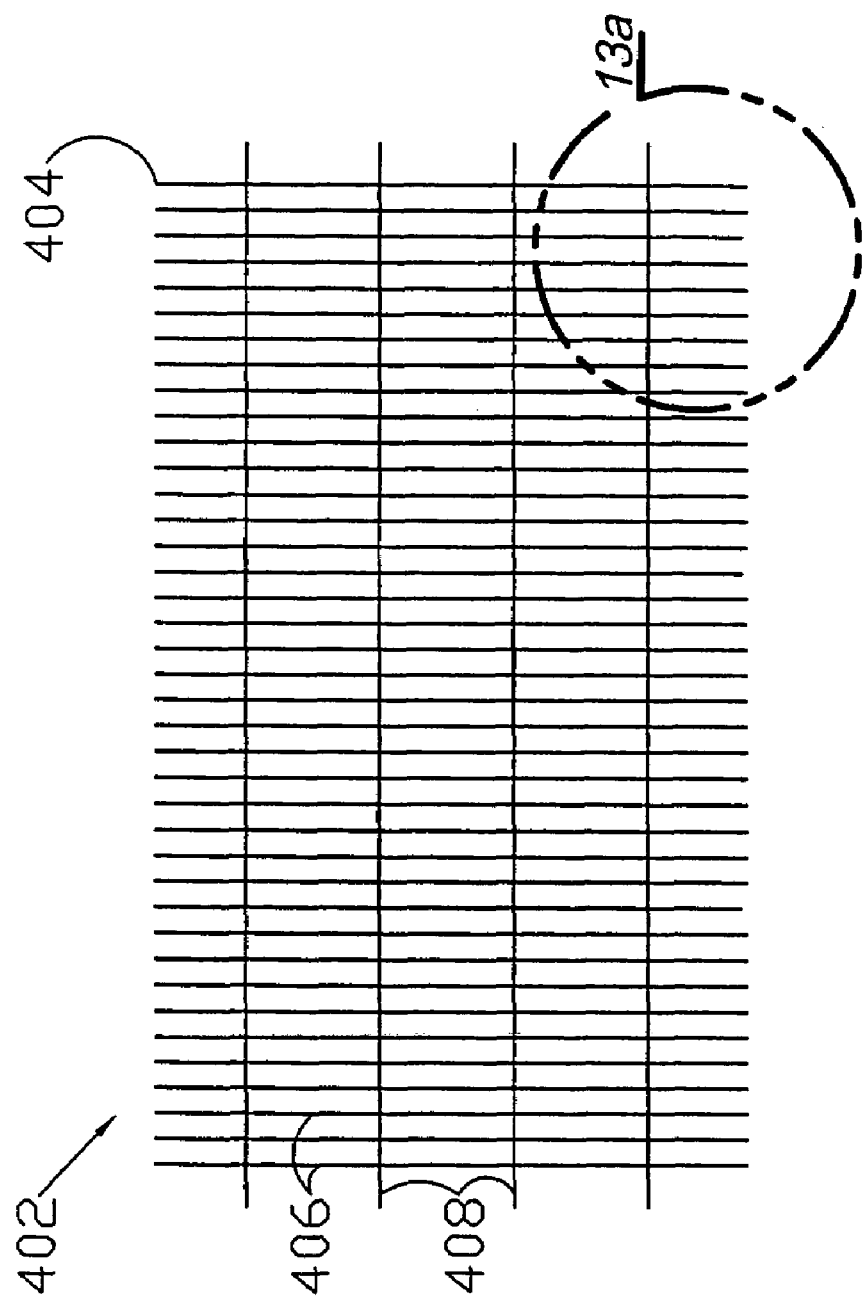
FIG. 12 is a side elevational view of a screen-only closure screen comprising an alternative embodiment of the present invention.
Figure 13B:
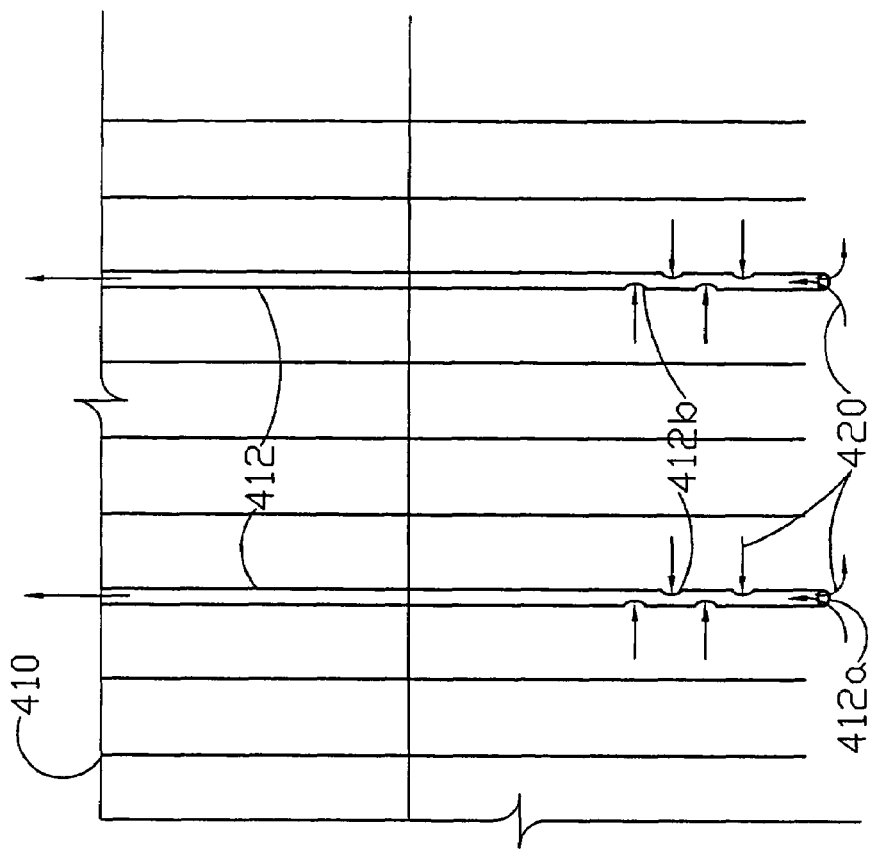
FIG. 13b is an enlarged, fragmentary, side elevational view thereof, showing modified vertical risers.
Figure 13A:
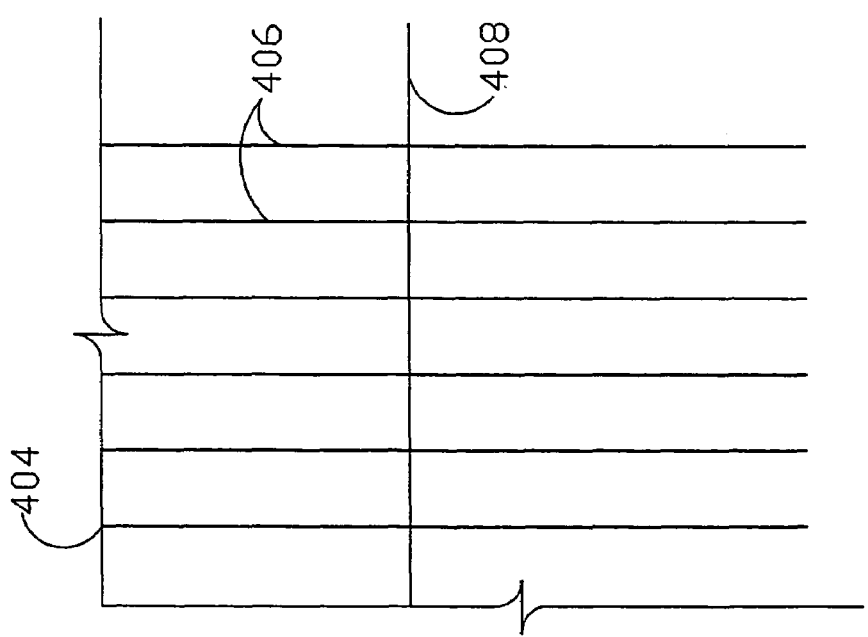
FIG. 13a is an enlarged, fragmentary, side elevational view thereof, taken generally within circle 13a in FIG. 12.

FIGS. 12, 13a and 13b show a modified embodiment screen-only closure screen system 402 and application methodology. A screen or mesh 404, similar to the screen 14 with barbed strands 30 described above, is placed in a separation 4 against the first tissue portion 12a. The second tissue portion 12b is then placed against the screen 404 whereby the separation 4 is closed and can be secured by the mechanical action of the screen 404. The screen 404 can be supplemented with sutures, drainage tubing, I/O devices, and other auxiliary components for purposes of closing the wound edges 12, draining the inside of the tissue separation 4, fighting infection, pain management and all other functionalities associated with the present invention, as discussed elsewhere herein. For example, the screen 404 can be secured with sutures at the subcutaneous level 8. Various fluid interconnecting devices can be utilized as necessary, and can be designed for removal after they serve their initial purpose. External drainage can also be achieved at the dermis level 6 utilizing transfer element subassemblies, such as the example designated 59 and described above (FIG. 7d). Moreover, drainage and irrigation tubing can be installed within the wound 4 alongside or adjacent to the screen 404. It will be appreciated that a screen-only version of the invention can comprise various suitable biocompatible absorbable and non-absorbable materials, including the materials disclosed above.

FIG. 13a is an enlarged view of the screen 404 and particularly shows barbed strands 406 and horizontal spacers 408, which are connected together in a grid pattern forming the screen 404. FIG. 13b shows an alternative embodiment with a modified screen 410 including vertical risers 412 comprising hollow tubing, which are connected to and spaced by horizontal spacers 408. Fluid flows into and out of the vertical risers 412 through open riser ends 412a and perforations 412b, as indicated by the fluid flow arrows 420.

Figure 14A:
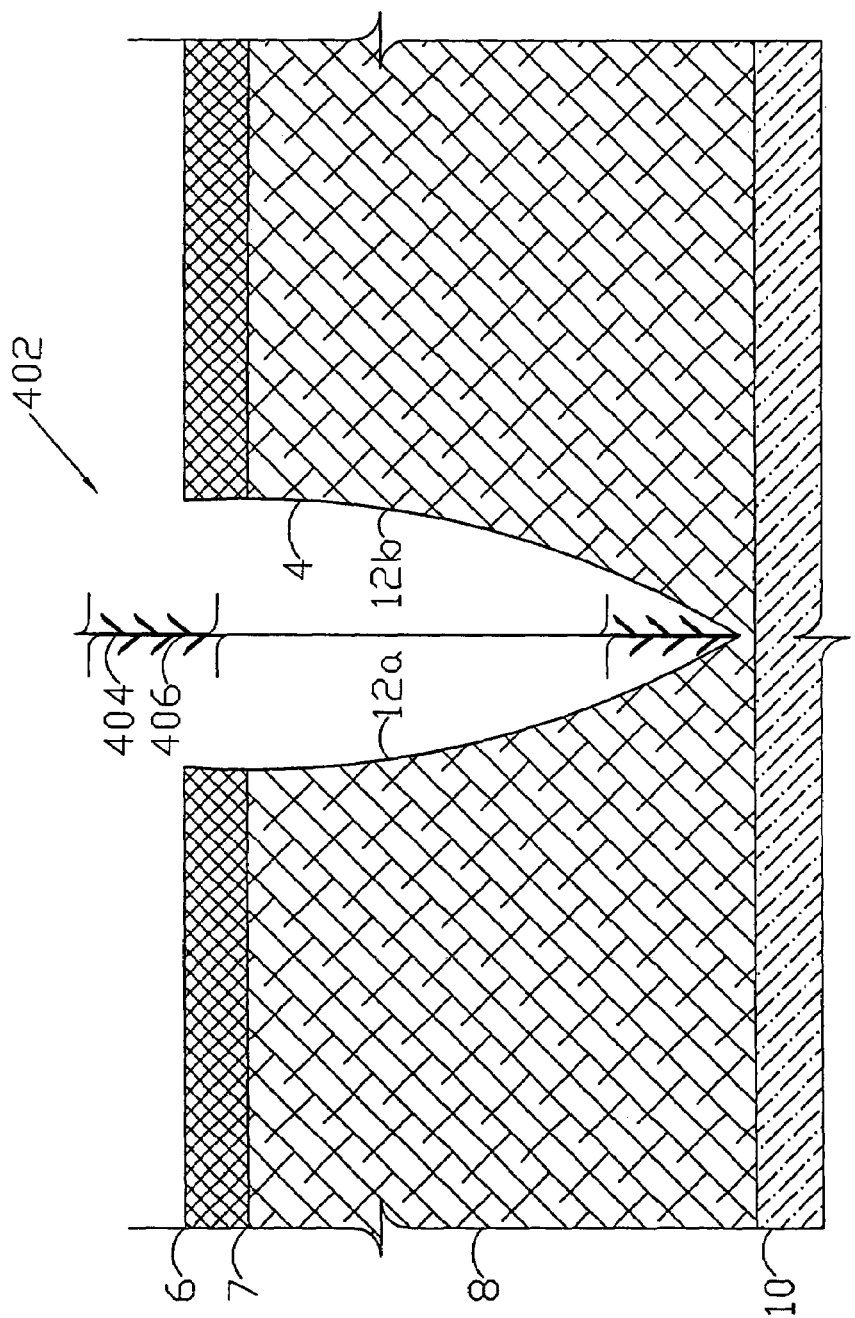
Figure 14B:
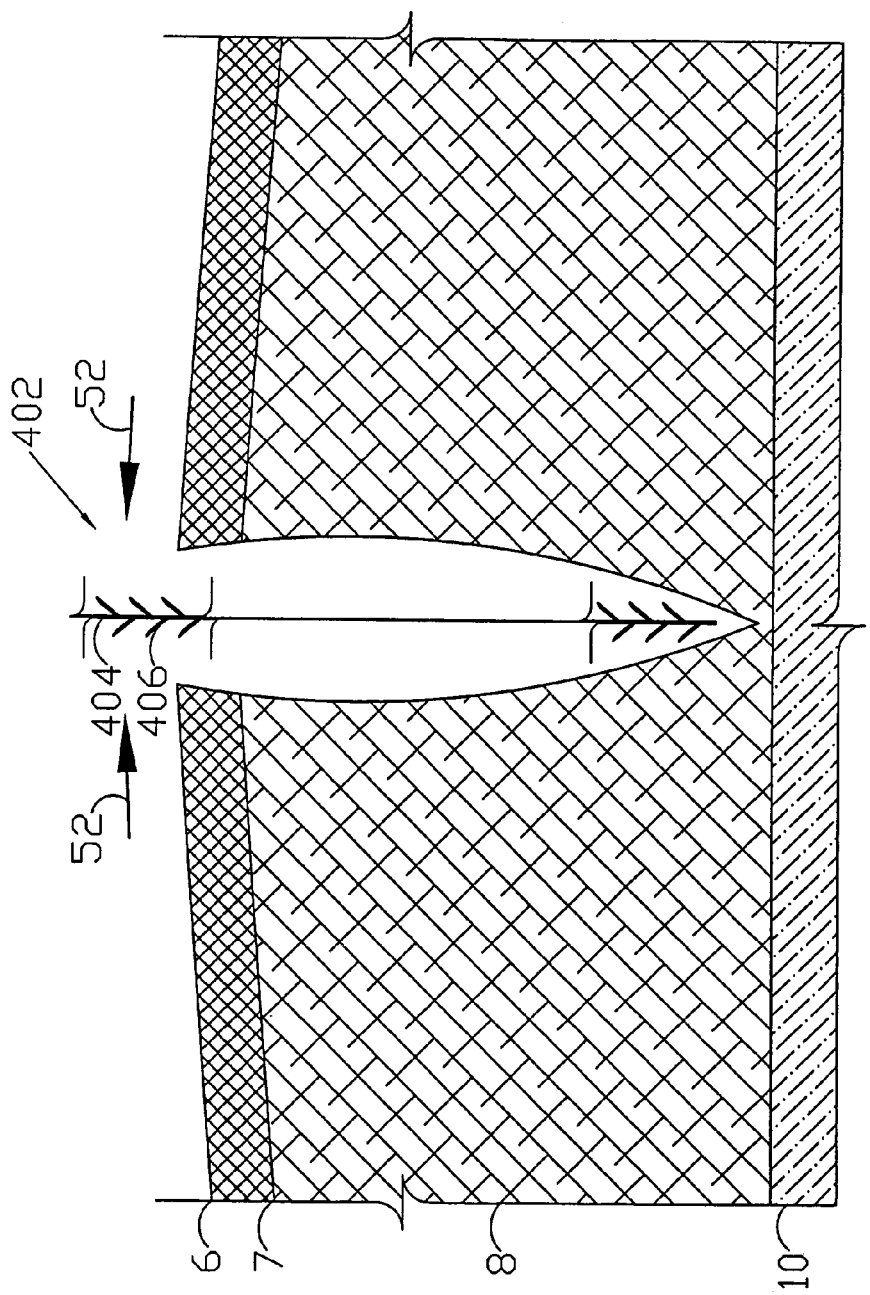
Figure 14C:
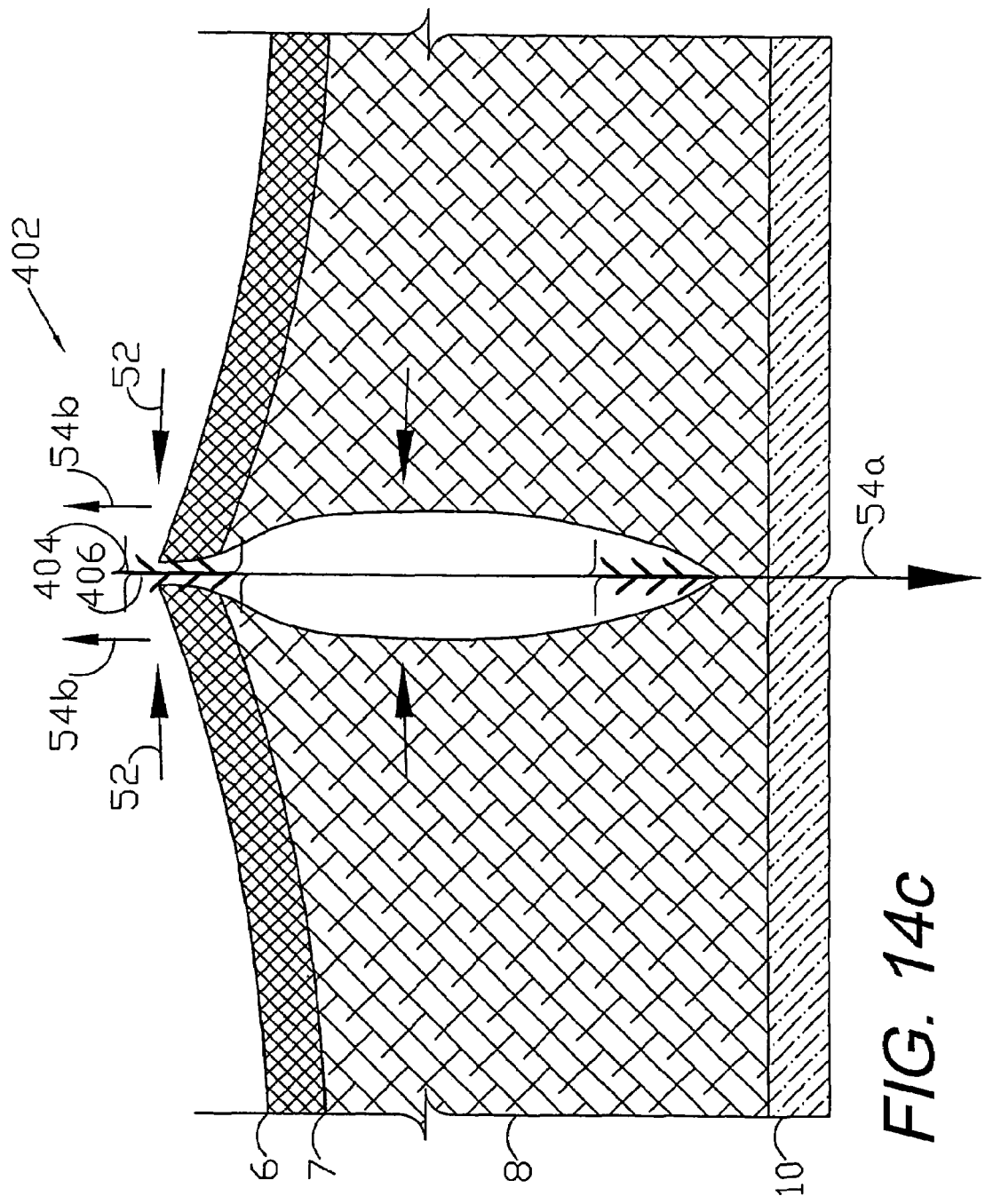
Figure 14D:
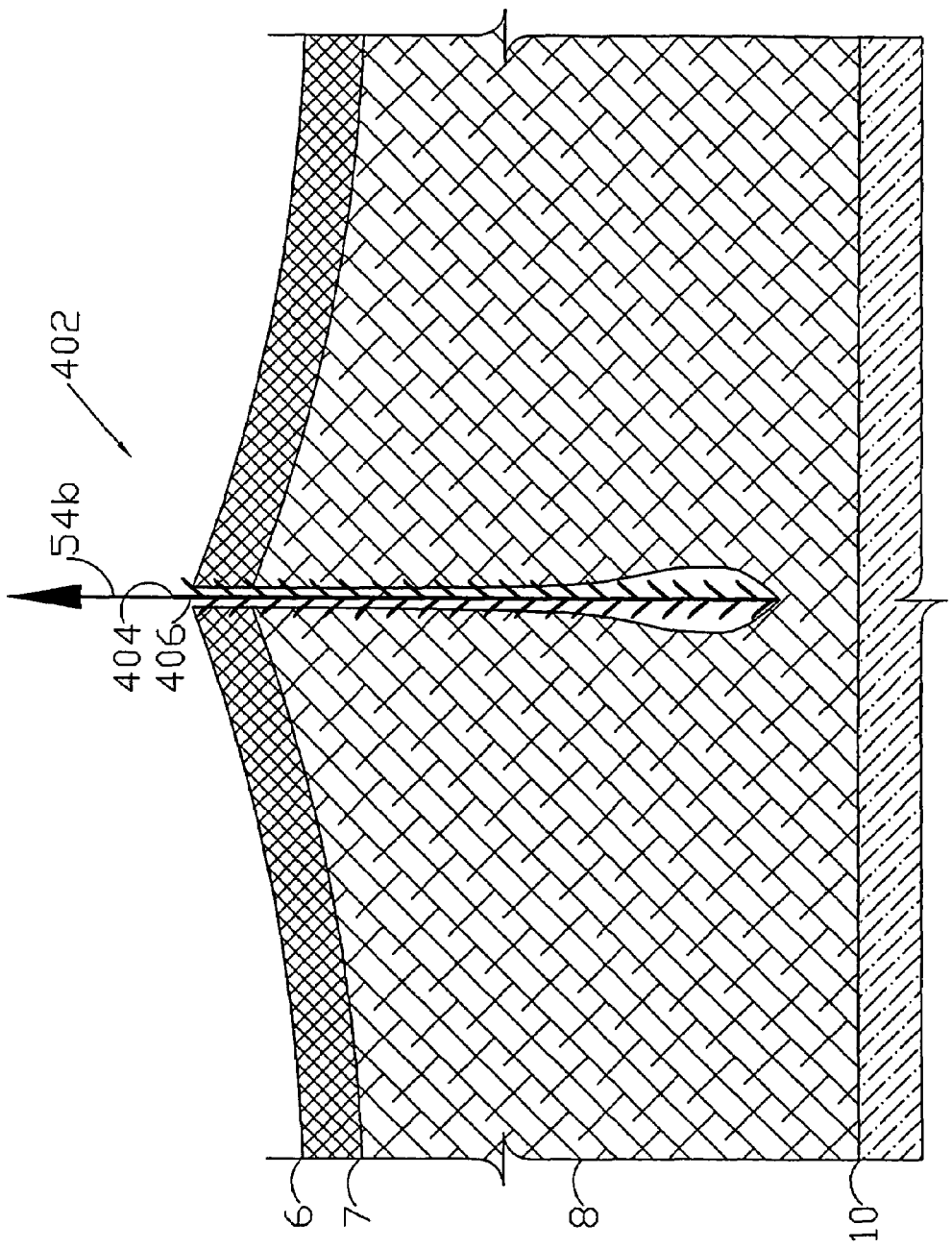
Figure 14E:
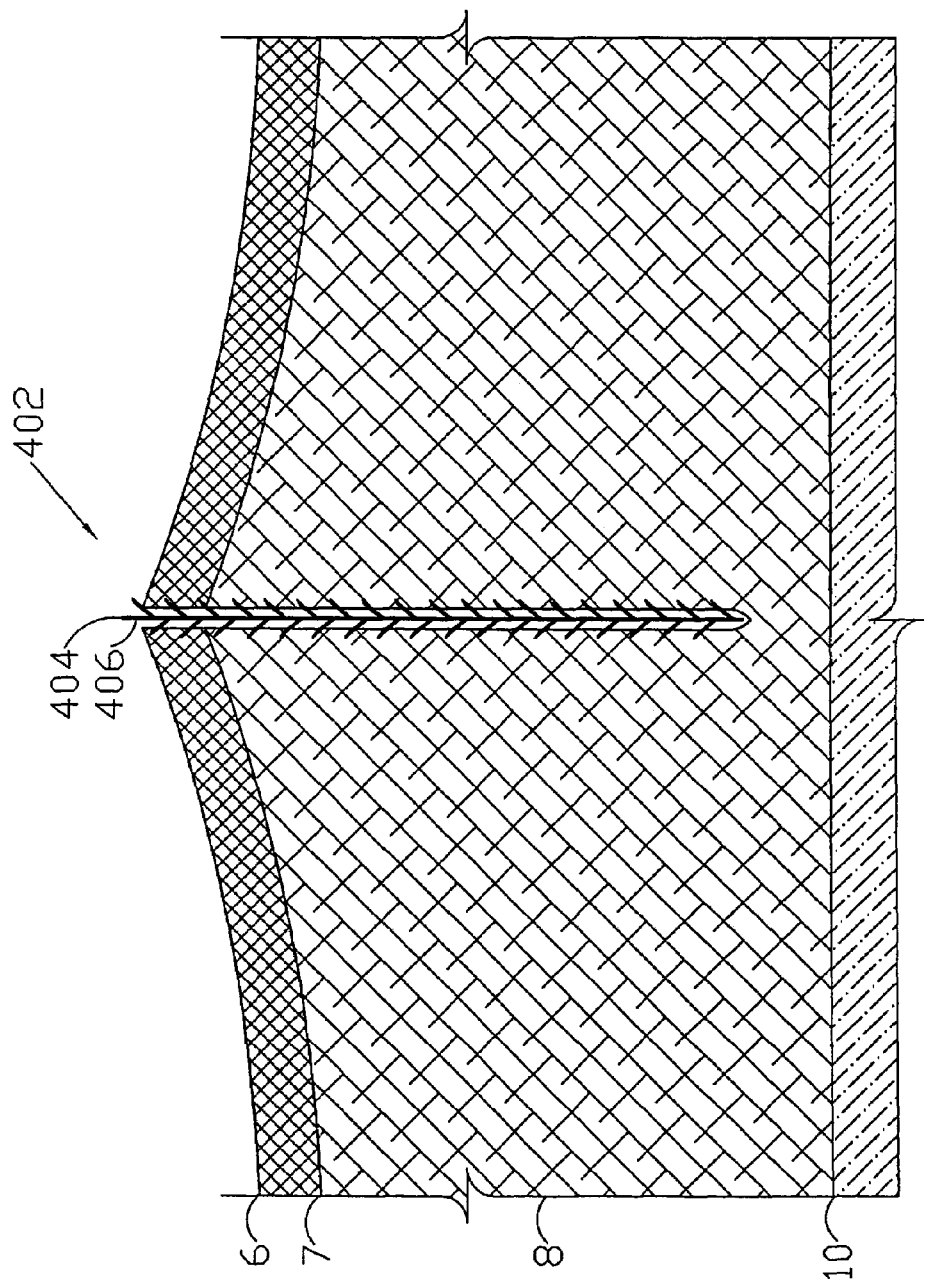

FIGS. 14a-g show the screen 404 installed in a tissue separation 4 and closing same, utilizing the methodology of the present invention. The methodology shown in FIGS. 14a-g is similar to the methodology shown in FIGS. 5a-e and 6a,b. FIG. 14c shows a downward/inward force arrow 54a indicating a direction in which the screen 404 is pushed or guided into the separation.

FIGS. 15a,b and 16a,b show a modified vertical riser 502 comprising bundled tubes 504 secured together at spaced intervals by connectors 506. The normal movement of the patient tends to alternately compress and expand the vertical risers 502, thus providing a "pumping" action for transferring fluid from the wound 4, as indicated by the fluid flow arrows 510. FIGS. 15a,b show a riser 502 in an extended configuration. Compressing the screen 14 longitudinally (i.e., end-to-end) compresses the bundled risers 504 to the configuration shown in FIGS. 16a,b, whereby fluid is drawn into the interstitial space 508 and pumped therefrom when the risers 502 extend.

FIG. 17 shows yet another configuration of a vertical riser 602 with bundled tubes 604, which are closely bunched and define passages 606 for conveying fluid. Such fluid conveyance can be enhanced by a pumping action associated with normal patient movements. Barbs 608 project outwardly from the tubes 604. It will be appreciated that various other bundled tube configurations, such as twisted, braided, etc., can be utilized.

Figure 18:
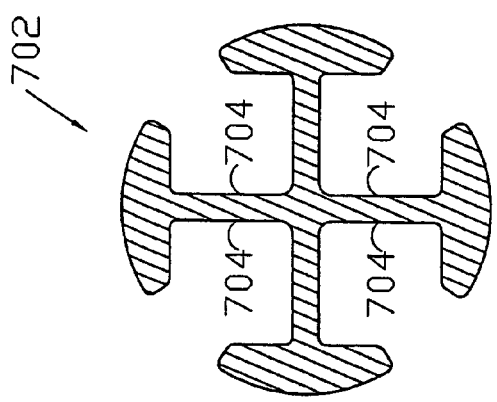
FIG. 18 is a cross-sectional view of a modified vertical riser or perimeter element, comprising a fluted tube.

FIG. 18 shows yet another vertical riser/perimeter member 702 alternative embodiment configuration. The member 702 has a configuration which is commonly referred to as a "fluted" drain and includes longitudinally-extending passages 704. This configuration can substitute for the perimeter members described above and can function to communicate fluid to and from the wound 4 with the input/output subsystem 18.

As additional alternative embodiment configurations for the vertical risers, they can comprise either barbed monofilament strands, similar to strand 30 shown in FIG. 3, or unbarbed monofilament strands. Such monofilament vertical risers can function as passive drains with fluid flowing alongside same. They can extend above the dermis 6 and abut or connect to transfer elements formed in various configurations with suitable absorbent materials. Examples include gauze dressings and transfer element subassemblies, such as 59 shown in FIG. 7d.

Figure 19:
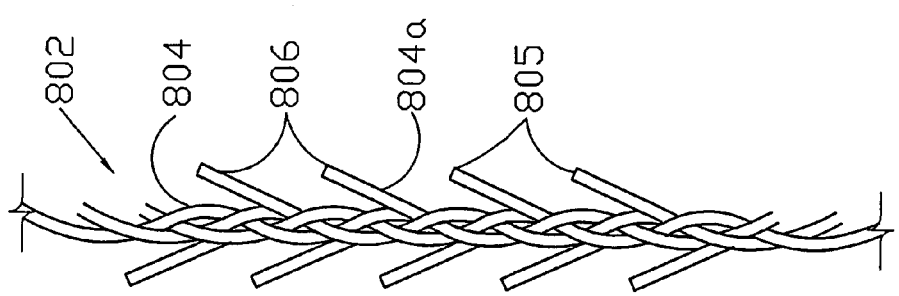
FIG. 19 is an enlarged, fragmentary, side elevational view of a modified barbed strand configuration.

FIG. 19 shows an alternative embodiment strand 802 constructed by twisting and braiding multiple, individual filaments 804. Barbs 805 are formed by respective individual filaments 804a, which terminate at blunt ends 806. The barbs 805 project generally outwardly from the strand 802 and form acute angles with respect to its longitudinal axis. They are adapted for penetrating tissue within a separation 4, as described above. In use, the barbs 805 would normally be oriented in directions generally pointing outwardly from the patient and the tissue separation 4.

Figure 20:
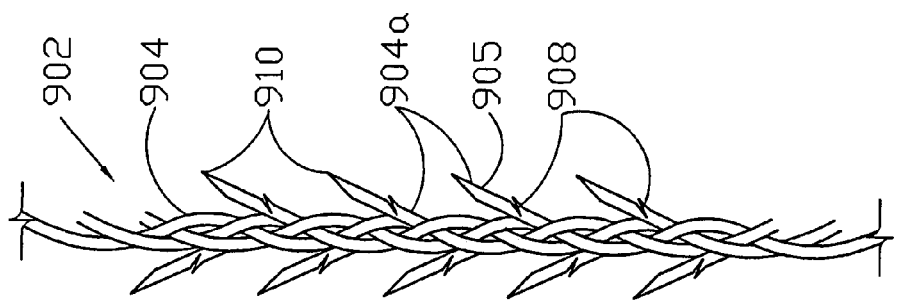
FIG. 20 is an enlarged, fragmentary, side elevational view of another modified barbed strand configuration.

FIG. 20 shows another alternative embodiment strand 902 comprising multiple twisted and braided filaments 904. Barbs 905 are formed from individual filaments 904a and have notches 908 and pointed ends 910. The notches 908 and the ends 910 are configured to allow the barbs 905 to easily extract from the separation edge tissues, whereby the screen is adapted for sliding along the separation edges in order to achieve the proper position.

FIG. 21 shows a further modified screen 1002 with barbs 1004 formed by looping individual filaments 1006 and cutting same at cut locations 1010 spaced inwardly from respective apexes 1008 of the filament loops. In operation, the barbs 1004 slightly penetrate the tissue and are imbedded therein. It will be appreciated that the filaments 1006 are relatively thin in diameter, similar to microfibers, whereby patient comfort is optimized.

FIG. 22 shows yet another modified screen 1102 with barbs 1104 formed by looping individual filaments 1106 and cutting-same at locations 1110 spaced inwardly from respective apexes 1108 of the filament loops whereby respective hooks 1112 are formed. The hooks 1112 operate in a manner similar to hook-and-loop fasteners, with the adjacent tissue forming the loop parts of the connections. In operation, the hooks 1112 slightly penetrate the tissue and are imbedded therein. The configurations of the hooks 1112 tend to retain them in the tissue adjacent to the separation 4 whereby the separated first and second tissue portions 12a,b can be closed.

FIG. 23 shows a screen 1202 with a configuration similar to the screen 1002 discussed above, with additional fiber elements or filaments 1204. The additional filaments 1204 tend to lay the filament barbs 1206 over whereby the screen 1202 can be directionally oriented within the wound separation 4 and operate in a manner similar to the screen 14 described above. The barbs 1206 are formed by cutting the apexes 1208 at cut locations 1210.

Similarly, FIG. 24 shows a screen 1302 with additional filaments 1304, which engage the filament loops 1306 and orient same in a direction towards the right as shown in FIG. 24. The slanted orientations of the filament loops 1306 facilitate setting same in the tissue portions 12a,b adjacent to the separation 4 by tugging outwardly on the screen 1302. Repositioning the screen 1302 is also possible, as described above. The filament loops 1306 can be cut at cut locations 1310, which are spaced inwardly from filament loop apexes 1308 whereby hooks 1312 are formed.

It will be appreciated that FIGS. 21-24 disclose screens with barbs and hooks extending from one face thereof. The present invention also includes screens with barbs and hooks extending from both faces.

FIGS. 25-27 show a closure screen 1702 including multiple, flexible barbed suture strands 1704 on a flexible mesh matrix 1706. Each strand 1704 has a half-round cross-sectional configuration with an outer, smooth, flat side 1708 and an inner, convex, barbed side 1710 including multiple notches 1712 forming barbs 1714, which can be oriented in opposite directions towards a medial point 1718, as shown in FIG. 26. If smoothness on the strand outer sides 1708 is not a necessary or critical requirement for a particular tissue closure, for ease of manufacturing the strands 1704 can be round or, alternatively, some of the prongs can be removed or covered with a suitable coating material to smooth a particular surface of the screen, whereby tissue penetration is accomplished with the remaining prongs.

Figure 30:
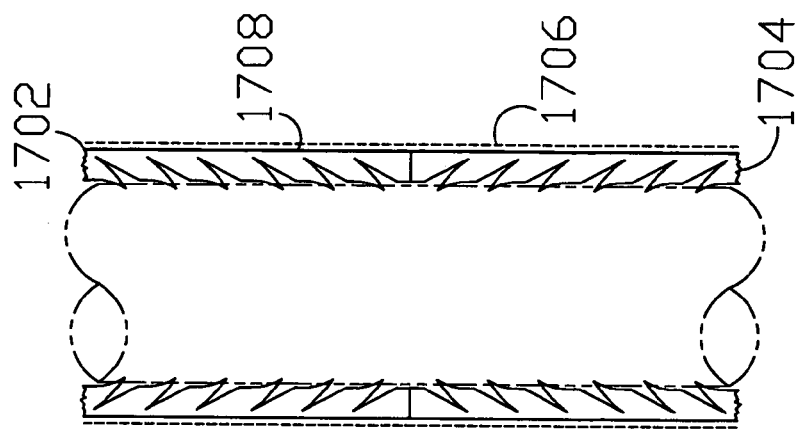
FIG. 30 is a fragmentary, side elevational view showing the divided structure substantially healed within the barbed strand system.
Figure 29:
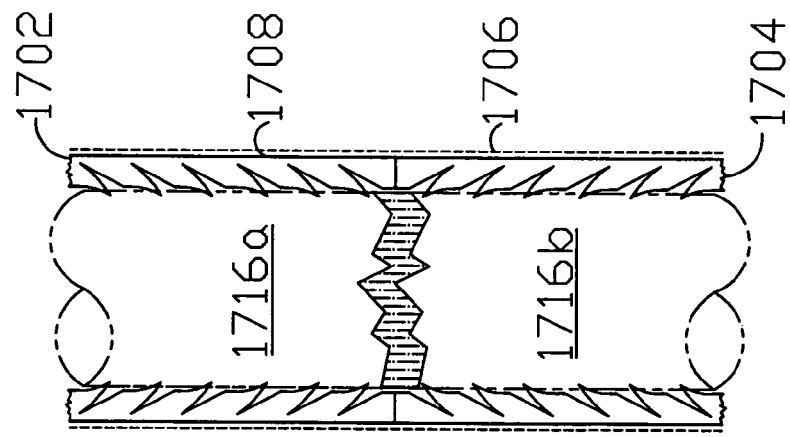
FIG. 29 is a fragmentary, side elevational view showing the divided structure substantially approximated within the barbed strand system.
Figure 28:
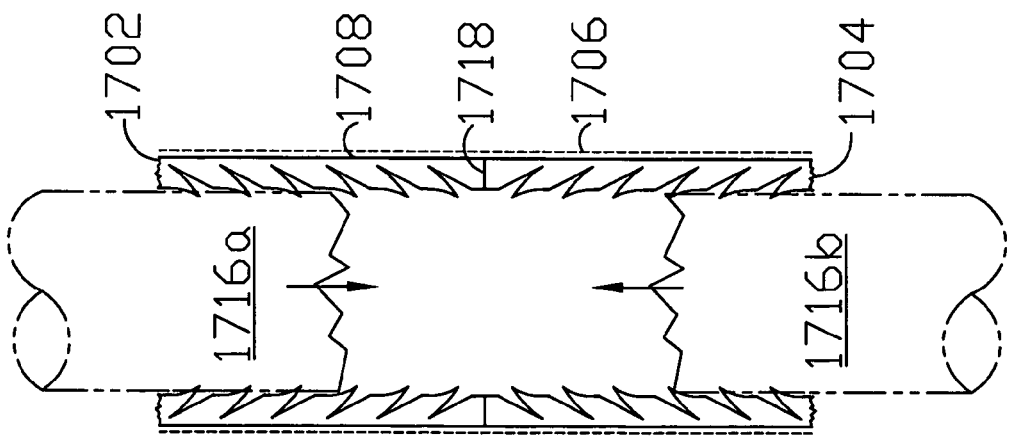
FIG. 28 is a fragmentary, side elevational view showing a divided tendon, nerve, blood vessel or similar structure received by the barbed strand system.

The barbs 1714 generally resist slippage of engaged tissue in one direction. The flexible matrix 1706 facilitates conforming the closure screen 1702 to irregular tissue shapes, and also enables wrapping the closure screen 1702 around a tendon, nerve or blood vessel in order to promote securing same. For example, FIGS. 28-32 show such an elongated tissue member 1716 being reconnected. The separated tissue portions 1716a,b can be positioned as shown in FIG. 28. The closure screen 1702 can then be wrapped around them. Alternatively, the closure screens can be manufactured in a choice of various diameters and tube shapes. The closure screens can be sized to the tissue and the appropriate sizes can be selected for use in the operating room. The separated tissue portions 1716a,b are inserted into the tube formed by the closure screen 1702 to approximately the location of the medial mark 1718. By approximating the tissue ends 1716a, b, as shown in FIG. 29, the one-way restraining action of the respective portions of the strands 1704 cooperate to resist pullout. Suitable pharmacologicals can be applied to the separated tissue portions 1716a,b to promote healing, nerve regeneration, tendon reattachment, etc. Alternatively, such pharmacologicals can be incorporated into the screen itself, which could then act as the delivery system for same. FIG. 30 shows the tendon, nerve or blood vessel substantially healed. FIG. 31 shows wrapped, tubular-shaped closure screens 1702 located inside (i.e. as a stent application) and/or outside of a separated blood vessel for closing same.

FIG. 31a shows an alternative embodiment closure screen 1720 with barbs 1722 oriented inwardly for engaging the outer wall of a proximal blood vessel segment 1724 within a proximal section 1726 of the closure screen 1720. Barbs 1728 are oriented outwardly for engaging the inner wall of a distal blood vessel segment 1730, which receives a distal section 1732 of the closure screen 1720. The closure screen 1720 can be installed to provide overlap of the blood vessel segments 1724, 1730. For example, the closure screen 1720 can be constructed as a compressible spring recoil filament matrix allowing compression and placement in the distal blood vessel segment 1730. The release of the closure screen 1720, functioning as a stent, dilates the vessel segment 1730 and reexpands the closure screen 1720, thereby allowing sliding insertion of the proximal blood vessel segment 1724 into the inside of the closure screen 1720 into an overlapping position with the distal blood vessel segment 1730. Suture reinforcement can be easily applied if additional security is required for this stent-type application, which can be made of permanent material such as titanium or a bioabsorbable material.

FIG. 32 shows another alternative embodiment closure screen 1740 with a necked-down, reducing configuration adapted to fit on the outside of a proximal blood vessel portion 1724 and on the inside of a distal blood vessel portion 1730. "Circumferential" refers to both the outer and inner circumferences of the blood vessels, such as 1716a,b by incorporation in 1702 as a delivery system. For example, all of the installations of the closure screens 1702, 1720 and 1740 shown in FIGS. 31, 31a and 32 are circumferential relative to the blood vessels 1716a,b and the passages through them.

The mesh 1706 can be finely or densely woven in order to achieve desired characteristics in the closure, such as weaving the mesh densely enough to make it water or tissue impermeable, thus allowing separation of cell activity from different tissue types on both sides of the screen, such as would be desirable in nerve repair. The density or open space of the weave can also be manipulated and opened more widely to allow vascular in-growth, for example, to a tendon graft. The same notched-strand closure pattern can be more densely woven for tendon repair to prevent vascular in-growth or adhesion formation to a native vascularized tendon repair without intervening graft.

Alternatively, the fine longitudinal suture strands 1704 can be used with a wide spacing mesh and wrapped first around one end of, for example, a nerve repair and then this entire unit placed inside an intact tubular structure, such as the available nerve regeneration tubules of specifically designed material to stimulate and contain nerve regeneration. For example, NeuraGen™ absorbable implant nerve guides are available from Integra NeuroSciences of Plainsboro, N.J. 08536, and can be used with the mesh 1706 in connection with nerve regeneration and similar procedures.

The second end of the nerve can then be placed inside this regeneration tubule and into the closure screen, which has the woven strands and mesh already circularly fixed around the first nerve end. The two nerve ends can be slid to the center point as previously described, thus fixating and engaging them inside the nerve regeneration tubule. Alternatively, the nerve regeneration tubule itself can be made incorporating the suture strands in it. This replaces or eliminates the currently required step of suturing to secure the nerve ends in a NeuraGen™ tube.

In addition to biodegradable materials, as discussed above, the components of the closure devices can comprise various other suitable materials. For example, metals such as stainless steel, titanium and platinum alloys can be employed for their desired characteristics of stiffness, strength, corrosion resistance and inertness (biocompatibility) with tissue. Coupled with the high degree of flexibility provided by the chain-like strands and the gossamer-like connecting filaments, the closure screens can be produced with a high degree of flexibility for patient comfort, as well as compatibility. For example, closure screens fabricated from metals for permanent placement will tend to be incorporated into the adjacent tissues, thus potentially reducing or eliminating patient discomfort. Alternatively, the prongs and the clip portions of the closure screen or strip can be non-absorbable, while the vertical risers, spacers and mesh-base can all be absorbable, leaving the staples or clip-like metal fasteners in place permanently.

FIGS. 33-36 show a circumferential closure device 2002 with a generally tubular configuration and adapted for repairing severed, linear tissue segments 1716a,b, which can be inserted into the open ends of the device 2002 (FIG. 34). The device 2002 is shown with a double helical construction with individual strands 2004 forming clockwise and counterclockwise helixes. With the tissue ends 1716a,b approximated (FIG. 34), the prongs 2006 engage the tissue ends 1716a,b and resist pullout. As shown in FIG. 36, the prongs 2006 are multi-directional and are oppositely-oriented at opposite ends of each strand 2004. Thus, a midpoint of the device 2002 is located approximately midway between the separated tissue ends 1716a,b. Pullout tension on the tissue ends 1716a,b tends to tighten the device 2002 thereon due to its double-helical construction, whereby further resistance to pullout is provided (FIG. 35).

FIG. 36a shows another alternative strand 2052 with primary and auxiliary lines 2054, 2056 positioned in generally parallel, juxtaposed sliding relation with prongs 2058 connected to and projecting outwardly from the primary lines 2054. The auxiliary lines 2056 can be either directly connected to the prongs 2058, or adapted for selective engagement, for example, when the auxiliary lines 2056 are linearly slid with respect to the primary lines 2054, as indicated by the sliding force arrow 2060. The generally parallel primary and auxiliary lines 2054, 2056 tend to support the prongs 2058 in predetermined positions and orientations, thus strengthening the strands 2052 whereby they resist buckling and breakage. The strands 2052 can thus be relatively thin and strong, with strength and rigidity characteristics that would require greater thicknesses in single-line constructions. Moreover, the alternative strands 2052 are adapted for helical-type circumferential closure devices, such as those shown in FIGS. 33-35. The relative sliding feature of the primary and auxiliary lines 2054, 2056 can be utilized to impart a torque rotating force indicated by a torque arrow 2062. Thus, a circumferential closure device such as that shown in FIGS. 33-35 can be initially positioned, for example around a tendon, and by sliding the auxiliary lines 2056 the prongs 2058 can be repositioned, reinforced and reoriented at suitable angles for tissue penetration and retention.

FIG. 37 shows another alternative embodiment closure device 2102 with a generally tubular configuration and multiple prongs 2104 oppositely-oriented at opposite ends of the device 2102. FIGS. 38 and 39 show yet another alternative embodiment closure device 2202 with oppositely-oriented, annular ridges 2204 oriented in opposite directions at opposite ends of the device 2202 (FIG. 39). The devices 2102 and 2202 perform in a substantially similar manner to the tubular device 2002 described above.

It is to be understood that while certain forms of the present invention have been illustrated and described herein, it is not to be limited to the specific forms or arrangement of parts described and shown.

Having thus described the invention, what is claimed as new and desired to be secured by Letters Patent is:

1. A tubular, circumferential medical closure device for closing a separation between first and second tissue portions, which device includes:
   a flexible screen having opposite first and second open ends, a longitudinal axis extending between said ends, multiple strands extending generally parallel to the longitudinal axis along substantially the entire length of said device between said screen ends;
   said strands being adapted for forming a circumferential configuration;
   each said strand including first, smooth face and a second, convex face presenting a semi-circular or semi-elliptical cross-sectional configuration of said strand; and
   each said strand also including multiple prongs positioned in spaced relation along substantially the entire length of said device intermediate said screen ends, at least some of said prongs being located intermediate said screen ends, said prongs projecting from the convex face of said strand and adapted for penetrating tissue.

2. The device according to claim 1, which includes:
   said prongs having multiple orientations with respect to said strands.

3. The device according to claim 1, which includes:
   an externally-applied vacuum dressing connected to said screen; and
   a negative pressure source connected to said dressing.

4. The device according to claim 1, which includes:
   prongs oriented both inwardly and outwardly with respect to said screen;
   said device being adapted to receive a first elongated tissue portion therein with said inwardly-oriented prongs engaging same; and
   said device being adapted to be received in a second elongated tissue portion with said outwardly-oriented prongs engaging same.

5. The device according to claim 1 wherein each said strand includes:
   primary and secondary lines positioned in generally parallel, juxtaposed sliding relation with respect to each other;
   multiple prongs mounted on said primary line; and
   said prongs being adapted for engagement by said secondary line whereby said prongs can be reoriented by sliding said lines relative to each other.

6. The device according to claim 1, which includes:
   a passage extending between and open at said ends; and
   said prongs comprising first and second sets of teeth adjacent to and oriented inwardly from said first and second ends respectively, said prongs projecting into said passage.

7. A method of circumferentially closing a separation between first and second tissue portions, which method comprises the steps of:
   providing a generally tubular flexible screen with opposite first and second open ends and a longitudinal axis extending between said screen ends;
   providing said screen with multiple strands extending generally parallel to the longitudinal axis along substantially the entire length of said screen between said screen ends;
   each said strand including a first, smooth face and a second, convex face presenting a semi-cirular or semi-elliptical configuration of said strand;
   approximating said first and second tissue portions;
   configuring and positioning said screen circumferentially with respect to said tissue portions;
   providing each said strand with multiple prongs positioned in spaced relation along substantially the entire length of said device intermediate said screen ends; and
   penetrating said first and second tissue portions with said prongs.

8. The method according to claim 7, which includes the additional steps of:
   wrapping said screen around said approximated tissue portions;
   trimming or overlapping excess screen material;
   releasing said tissue portions;
   placing said screen in tension; and
   fastening said screen in a tubular configuration either receiving or received by said tissue portions, or both.

9. The method according to claim 7, which includes the additional steps of:
   preforming said screen in a tubular configuration; and
   inserting one or both of said tissue portions into said screen and/or inserting said screen into one or both of said tissue portions.

10. The method according to claim 7, which includes the additional steps of:
    stabilizing and compressing the tissue portions and the device with an externally-applied vacuum dressing to maintain the embedded prong position against increasing distraction load on the prongs and to improve the efficiency of the system.

11. The method according to claim 7, which includes the additional steps of:
    providing each said strand with generally parallel, adjacent primary and auxiliary lines;
    connecting said prongs to said primary lines;
    sliding said primary and auxiliary lines relative to each other;
    engaging said prongs with said auxiliary lines; and
    reorienting said prongs relative to said primary lines.

12. A tubular, circumferential medical closure device for closing a separation between first and second tissue portions, which device includes:
    a flexible screen having opposite first and second open ends, a longitudinal axis extending between said ends and multiple strands extending generally parallel to the longitudinal axis along substantially the entire length of said device between said device ends;

said strands being adapted for forming a generally tubular, circumferential configuration;

each said strand including a first, smooth face and a second, convex face presenting a semi-circular or semi-elliptical cross-sectional configuration of said strand;

each said strand including multiple prongs positioned in spaced relation along substantially the entire length of said device intermediate said device ends, at least some of said prongs being located intermediate said device ends;

an externally-applied vacuum dressing connected to said screen; and a negative pressure source connected to said dressing.

* * * * *